United States Patent [19]

Kampe et al.

[11] Patent Number: 4,859,670

[45] Date of Patent: Aug. 22, 1989

[54] 2-AZOLYLMETHYL-2-ARYL-1,3-DIOXO-LANES AND THE SALTS THEREOF, AGENTS CONTAINING SAME, AND THE USE THEREOF

[75] Inventors: Klaus-Dieter Kampe, Bad Soden am Taunus; Wolfgang Raether, Dreieich; Walter Dittmar, Hofheim am Taunus; Heinz Hänel, Bad Homburg, all of Fed. Rep. of Germany

[73] Assignee: Hoechst Aktiengesellschaft, Frankfurt am Main, Fed. Rep. of Germany

[21] Appl. No.: 28,193

[22] Filed: Mar. 19, 1987

[30] Foreign Application Priority Data

Mar. 21, 1986 [DE] Fed. Rep. of Germany ....... 3609598

[51] Int. Cl.$^4$ .................. A61K 31/505; C07D 405/14
[52] U.S. Cl. ...................................... 514/252; 544/295; 544/360; 544/363
[58] Field of Search .......................... 544/295; 514/252

[56] References Cited

U.S. PATENT DOCUMENTS

| | | | |
|---|---|---|---|
| 4,267,179 | 5/1981 | Heeres et al. | 514/252 |
| 4,287,195 | 9/1981 | Heeres et al. | 514/252 |
| 4,335,125 | 6/1982 | Heeres et al. | 514/252 |
| 4,358,449 | 11/1982 | Heeres et al. | 514/252 |
| 4,456,605 | 6/1984 | Heeres et al. | 514/252 |
| 4,619,931 | 10/1986 | Heeres et al. | 514/252 |
| 4,634,700 | 1/1987 | Schickaneder et al. | 514/252 |

*Primary Examiner*—Glennon H. Hollrah
*Assistant Examiner*—James H. Turnipseed
*Attorney, Agent, or Firm*—Finnegan, Henderson, Farabow, Garrett, & Dunner

[57] ABSTRACT

Compounds of the formula I

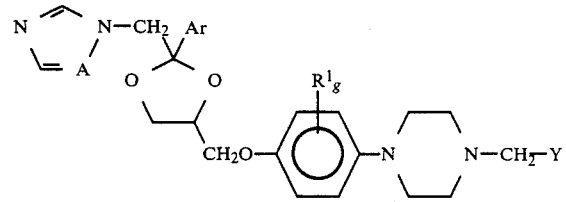

in which A equals CH or N, Ar equals phenyl, naphthyl or thienyl, $R^1$ equals alkyl or halogen, and Y is a number of nitrogen-containing heterocyclic rings, have an excellent antimycotic action.

The compounds IIIa

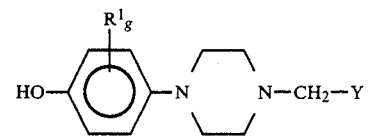

are valuable intermediates for the preparation thereof.

7 Claims, No Drawings

2-AZOLYLMETHYL-2-ARYL-1,3-DIOXOLANES AND THE SALTS THEREOF, AGENTS CONTAINING SAME, AND THE USE THEREOF

The invention relates to 2-azolylmethyl-2-aryl-4-[(4-piperazinophenoxy)methyl]-1,3-dioxolanes, including the salts thereof, which are substituted by heterocyclic rings, processes for the preparation thereof, medicaments containing these compounds, and the use thereof, particularly as antimycotics.

2-Azolylmethyl-2-aryl-4-[(4-piperazinophenoxy)methyl]-1,3-dioxolanes which have an antimycotic or fungicidal action are already known and are described, inter alia, in German Offenlegungsschrift No. 2,804,096 and European Offenlegungsschrift No. 7,696. The best known representatives from the large number of compounds described are 2-S,(R)(2,4-dichlorophenyl)-2-(imidazol-1-ylmethyl)-4-R,(S)-[4-(4-acetylpiperazin-1-yl)phenoxymethyl]-1,3-dioxolane (ketoconazole) and 2-S,(R)-(2,4-dichlorophenyl)-2-(1,2,4-triazol-1-ylmethyl)-4-R,(S)-[4-(4-isopropylpiperazin-1-yl)phenoxymethyl]-1,3-dioxolane (terconazole), which are commercially available as antimycotics (cf. German Offenlegungsschrift No. 2,804,096, Example 20 and Example 53), ketoconazole being used mainly as a systemically active antimycotic and terconazole as a topically active antimycotic. However, the antimycotic action and, in particular, the toleration of the known compounds are not always completely satisfactory.

It has now been found that 2-azolylmethyl-2-aryl-4-[(4-piperazinophenoxy)methyl]-1,3-dioxolanes of the formula

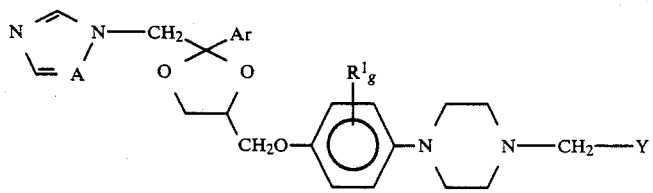

I in which
A denotes CH or N,
Ar denotes naphthyl, thienyl, halothienyl or a phenyl group which is unsubstituted or carries one to 3 substituents, where the substituents may be identical or different and denote F, Cl, Br, I, $CF_3$, $OCH_3$, $OC_2H_5$, $CH_3$, $C_2H_5$ or phenoxy,
$R^1$ denotes $C_1$–$C_3$-alkyl, F or Cl,
g denotes 0, 1 or 2 and
Y denotes on of the following heterocyclic radicals

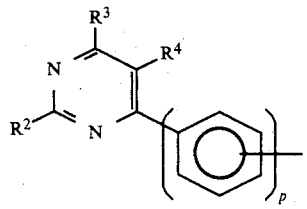

(a₁)

or

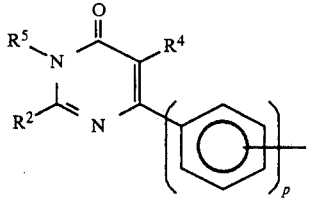

(a₂)

or

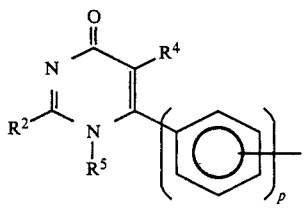

or

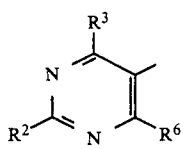

(b₁)

or (b₂)

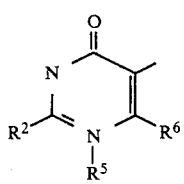

or

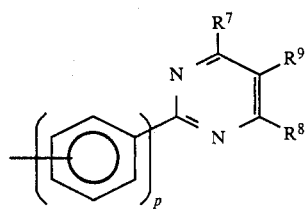

(c)

in which
$R^2$ denotes H, $C_1$–$C_8$-alkyl, $C_1$–$C_4$-alkoxy, a phenyl group which is unsubstituted or carries 1 or 2 substituents, where the substituents may be identical or different and denote F, Cl, Br, I, $CF_3$, $OCH_3$, $OC_2H_5$, $NO_2$ or $C_1-C_4$-alkyl, or a phenyl—$C_1-C_2$-alkyl group which is unsubstituted or carries 1 or 2 substituents in the phenyl radical, where the substituents may be identical or different and denote F, Cl, Br, $OC_2H_5$, $CH_3$ or $C_2H_5$, or, in the case of the radical $a_1$, additionally denotes $C_1-C_4$-alkylthio, or a benzylthio group which is unsubstituted or carries 1 or 2 substituents in the phenyl radical, where the substituents may be identical or different and denote F, Cl, $OCH_3$, $OC_2H_5$, $CH_3$ or $C_2H_5$, $R^3$ denotes H, OH, Cl, $C_1-C_4$-alkoxy or a benzyloxy group which is unsubstituted or carries 1 or 2 substituents in the phenyl radical, where the substituents may be identical or different and denote F, Cl, Br, $OCH_3$, $OC_2H_5$, $CH_3$ or $C_2H_5$, and, in the case of the heterocyclic radical $a_1$, additionally denotes $C_1-C_4$-alkyl or a phenyl group which is unsubstituted or substituted by one F, Cl, Br, $OCH_3$, $OC_2H_5$, $CH_3$ or $C_2H_5$ and, in the case of the heterocyclic radical $b_1$, additionally denotes $C_1-C_4$-alkyl or a phenyloxy group which is unsubstituted or carries 1 or 2 substituents, where the substituents may be identical or different and denote F, Cl, Br, $OCH_3$, $OC_2H_5$, $CH_3$ or $C_2H_5$, $R^4$ denotes H, Cl, Br, $C_1-C_4$-alkyl or CN, $R^5$ denotes H, $C_1-C_4$-alkyl, prop-2-en-1-yl, prop-2-in-1-yl of benzyl, p1 denotes 0 or 1, the phenylene radical in $a_1$, $a_2$ and c being bonded via the 2, 3 or 4 position, $R^6$ denotes H, $C_1-C_8$-alkyl, ($C_3-C_6$-cycloalkyl)-$C_{1-C3}$-alkyl, a phenyl group which is unsubstituted or carries 1 or 2 substituents, where the substituents may be identical or different and denote F, Cl, Br, I, $OCH_3$, $OC_2H_5$, 1,2—O—$CH_2$—O—, $CF_3$ or $C_1-C_4$-alkyl, a phenyl-$C_1-C_2$-alkyl group which is unsubstituted or substituted in the phenyl radical by $OCH_3$, $OC_2H_5$, 1,2—O—$CH_2$—O—, $CF_3$, F, Cl or $C_1-C_4$-alkyl, or $CF_3$, $R^7$ and $R^8$, independently of one another, denote H, $C_1-C_8$-alkyl, $C_1-C_4$-alkoxy or a phenyl or benzyl group which is unsubstituted or carries 1 or 2 substituents in the phenyl radical, where the substituents may be identical or different and denote F, Cl, Br, $OCH_3$ or $OC_2H_5$, and where, in addition, $R^7$ may alternatively denote OH, and $R^9$ denotes H, Cl, Br or CN, or Y denotes one of the following heterocyclic radicals

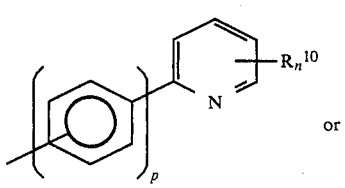
(d₁)

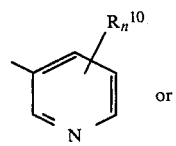
(d₂)

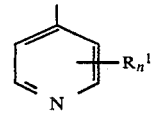
(d₃)

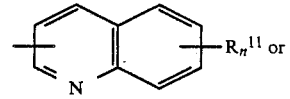
(d₄)

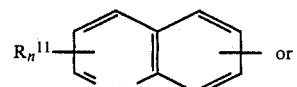
(d₅)

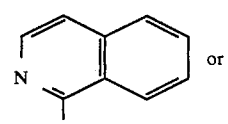
(d₆)

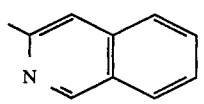
(d₇)

in which p1 denotes 0 or 1, $R^{10}$ denotes Cl, Br, $OCH_3$, $OC_2H_5$, $CH_3$ or $C_2H_5$, n denotes 0, 1 or 2, where may be in the 3, 4, 5 and/or 6 position in $d_1$, in the 2, 4, 5 and/or 6 position in $d_2$ and in the 2, 3, 5 and/or 6 position in $d_3$, and $R^{11}$ denotes Cl, $OCH_3$, $CH_3$ or $C_2H_5$, and may be in one or two of the free positions in $d_4$ and $d_5$, and the heterocyclic radical $d_4$ is bonded via the 2, 3 or 4 position, the heterocyclic radical $d_5$ is bonded via the 5, 6, 7 or 8 position and the phenylene unit in the radical $d_1$ is bonded via the 2, 3 or 4 (para) position, and the physiologically acceptable acid-addition salts thereof, have valuable antimycotic or fungicidal properties. They are therefore suitable for combating mycosis in humans and animals and for combating fungal infestations in plants and on materials.

In this context, the term "halothienyl" is taken to mean a thienyl radical which is linked in the 2 or 3 position and which may be substituted in any position by an F, Cl, Br or I atom, preferably Br or Cl, the terms "$C_1-C_3$-, $C_1-C_4$- and $C_1-C_8$-alkyl" are taken to mean an unbranched or branched hydrocarbon radical having 1-3, 1-4 or 1-8 carbon atoms respectively, the term "$C_3-C_6$- or $C_5-C_6$-cyclo-alkyl" is taken to mean a cyclopropyl, cyclobutyl, cyclopentyl or cyclohexyl radical or a cyclopentyl or cyclohexyl radical respectively, and the term "$C_1-C_4$-alkoxy" or "$C_1-C_4$-alkylthio" is taken to mean an alkoxy or alkylthio group respectively, the hydrocarbon radical of which has the meaning specified under the term "$C_1-C_4$-alkyl".

Preferred compounds of the formula I are those in which at least one of the substituents or indices has the following meaning:

A denotes CH or N,

Ar denotes a phenyl group which is substituted by 1 or 2 F or Cl atoms, $R^1$ denotes $CH_3$ or $C_2H_5$, g denotes 0 or 2, and, where Y denotes a heterocyclic radical $a_1$, $a_2$, $b_1$, $b_2$ or c:

$R^2$ denotes H, $C_1$–$C_4$-alkyl, $CH_3O$ or a phenyl or benzyl group which is unsubstituted or carries 1 or 2 substituents in the phenyl radical, where the substituents may be identical or different and denote F, Cl, Br or $OCH_3$, $R^3$ denotes H or $C_1$–$C_4$-alkoxy, and, in the case of the heterocyclic radical $a_1$, additionally denotes $CH_3$ or a phenyl group which is unsubstituted or substituted by one F, Cl, $OCH_3$ or $CH_3$, and, in the case of the radical $b_1$, additionally denotes a phenyloxy group which is unsubstituted or carries 1 or 2 substituents, where the substituents may be identical or different and denote F, Cl, Br, $OCH_3$ or $OC_2H_5$, $R^4$ denotes H or CN, and, in the case of the heterocyclic radical $a_1$, additionally denotes $C_1$–$C_4$-alkyl, $R^5$ denotes $CH_3$, p1 denotes 0 or 1, $R^6$ denotes H, $C_1$–$C_8$-alkyl, ($C_5$–$C_6$-cycloalkyl)-$C_1$–$C_2$-alkyl a phenyl group which is unsubstituted or carries 1 or 2 substituents, where the substituents may be identical or different and denote F, Cl, Br, $OCH_3$, $OC_2H_5$ or $CF_3$, a benzyl group which is unsubstituted or substituted in the phenyl radical by $OCH_3$, $CF_3$, F or Cl, or $CF_3$, $R^7$ and $R^8$, independently of one another, denote $C_1$–$C_8$-alkyl, $C_1$–$C_4$-alkoxy, or a phenyl or benzyl group which is unsubstituted or substituted in the phenyl radical by F, Cl, $OCH_3$ or $OC_2H_5$, and in addition, $R^7$ alternatively denotes H or OH, and $R^9$ denotes H or CN, or, where Y denotes a heterocyclic radical $d_1$, $d_2$, $d_3$, $d_4$, $d_5$, $d_6$ or $d_7$:

P denotes 0 or 1, $R^{10}$ denotes Cl, $CH_3$ or $C_2H_5$, n denotes 0 or 1, where, in $d_3$, $R^{10}$ is preferably in the 2 position, and $R^{11}$ denotes Cl, the phenylene unit in the $d_1$ radical preferably being bonded via the 4 position.

Particularly preferred compounds of the formula I are those in which at least one of the substituents or indices has the following meaning:

A denotes CH or N,

Ar denotes 2,4-dichlorophenyl, $R^1$ denotes $CH_3$, g denotes 0 or 2, and, where Y denotes a heterocyclic radical $a_1$, $a_2$, $b_1$, $b_2$ $R^2$ denotes $CH_3$, or a phenyl or benzyl group which is unsubstituted or carries 1 or 2 substituents in the phenyl radical, where the substituents may be identical or different and denote F or Cl, and, in the phenyl group, and in the phenyl and the benzyl group in the radical $a_1$, additionally denotes $OCH_3$, and, in the case of the radical $a_1$, additionally denotes $C_2$–$C_4$-alkyl, $R^3$, in the radical $a_1$, if p is 0, denotes $CH_3$, or a phenyl group which is unsubstituted or substituted by an F, Cl or $OCH_3$, and, if p is 1, denotes H, and, in the radical $b_1$, denotes H or a phenyloxy group which is unsubstituted or substituted by F, Cl, $OCH_3$ or $OC_2H_5$, $R^4$ denotes H, or, in the radical $a_1$, additionally denotes $CH_3$ if p is 0, $R^5$ denotes $CH_3$, P denotes 0 or 1 in the case of the heterocyclic radicals $a_1$ and $a_2$, and denotes 1 in the case of the heterocyclic radical c, $R^6$ denotes H, $CH_3$, or a phenyl group which is unsubstituted or monosubstituted by F, Cl, $OCH_3$ or $OC_2H_5$, $R^7$ and $R^8$, independently of one another, denote $CH_3$, or a phenyl group which is unsubstituted or substituted by F, Cl or $OCH_3$, and, in addition, $R^7$ alternatively denotes H or $C_1$–$C_4$-alkoxy, and $R^9$ denotes H, or where Y denotes a heterocyclic radical $d_1$, $d_2$, $d_3$, $d_4$, $d_5$, $d_6$ or $d_7$:

P denotes 0 or 1, and n denotes 0, the radical $d_4$ preferably being bonded via the 2 position and the radical $d_5$ preferably being bonded via the 6 or 7 position.

Compounds in which Y denotes the radical $d_6$ or $d_7$ are not particularly preferred.

The invention furthermore relates to the possible stereoisomers of the formula I, as diastereomer racemates and as pure enantiomers, and the pharmaceutically acceptable salts thereof. In particular, this relates to the stereoisomers which are possible as a result of the 2,4-disubstitution of the 1,3-dioxolane ring; the 2-azolylmethyl group may be located in the cis or trans position to the substituent in the 4 position, the substituted phenoxymethyl group. The cis isomers are included in the preferred compounds according to the invention.

Suitable salts of the compounds of the formula I according to the invention are those with physiologically acceptable inorganic and organic acids, such as, for example, hydrochloric acid, hydrobromic acid, hydroiodic acid, sulfuric acid, phosphoric acid, nitric acid, benzenesulfonic acid, toluenesulfonic acid, sulfamic acid, methylsulfuric acid, acetic acid, propionic acid, oleic acid, palmitic acid, stearic acid, malonic acid, maleic acid, succinic acid, glutaric acid, malic acid, tartaric acid, citric acid, fumaric acid, lactic acid, glycolic acid, pyruvic acid, benzoic acid, toluic acid, glutamic acid, furancarboxylic acid, salicylic acid or mandelic acid. Preferred salts are those with physiologically acceptable inorganic acids, strong to medium-strength acidic derivatives of such acids, or with fumaric acid.

The compounds according to the invention differ from the known, abovementioned azolylmethyl-2-aryl-4-[(4-piperazinophenoxy)methyl]-1,3-dioxolanes which are active against fungi and bacteria essentially through the type of the substituents on the piperazinophenoxymethyl unit in the 4 position of the dioxolane ring and through the additional substitution, optionally present, of the phenyl ring of the phenoxy group in the 4 position.

Surprisingly, the 2-azolyl-2-aryl-4-[(4-piperazinophenoxy)methyl]-1,3-dioxolanes according to the invention exhibit a broader and better antimycotic action than the known 2-azolylmethyl-2-aryl-1,3-dioxolane derivatives and the known 2-S,(R)-(2,4-dichlorophenyl)-2-(imidazol-1-ylmethyl)-4-R,(S)-[4-(4-acetyl-piperazin-1-yl)phenoxymethyl]-1,3-dioxolane (ketoconazole).

The invention furthermore relates to a process for the preparation of the compounds of the formula I and the salts thereof, wherein (A) a compound of the formula II

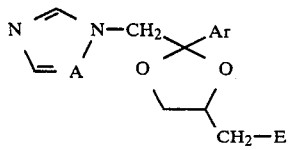

in which
- A and Ar have the meanings specified in the case of the formula I and
- E denotes halogen, such as F, Cl, Br or I, acyloxy, such as acetoxy, trifluoroacetyloxy, benzoyloxy or nitrobenzoyloxy, $C_1$–$C_3$-arylsulfonyloxy, such as methanesulfonyloxy, or arylsulfonyloxy, such as benzene-, nitrobenzene-, bromobenzene- or toluenesulfonyloxy, is reacted with a compound of the formula III

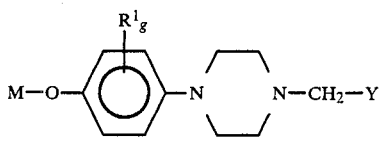

in which
- M denotes H, an alkali metal or an alkaline-earth metal, particularly Li, Na or K, or $NH_4$, and
- $R^1$, g and Y have the meanings specified in the case of the formula I, or wherein (B) a compound of the formula IV,

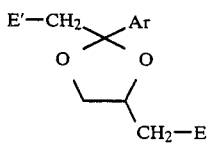

in which Ar has the meanings specified in the case of the formula I and E and E' have the meanings specified for E in the case of the formula II, is initially reacted with a compound of the formula III, a compound of the formula V,

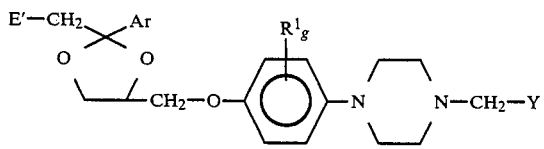

in which Ar, $R^1$, g and Y have the meanings specified in the case of the formula I, and E' has the meanings specified for E in the case of the formula II, being prepared here, and a compound of the formula V is subsequently reacted with a compound of the formula VI,

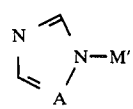

in which A denotes CH or N and M' denotes H, an alkali metal, an alkaline-earth metal or $Si(CH_3)_3$, or wherein (C) a compound of the formula VII,

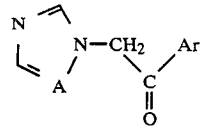

in which A and Ar have the meanings specified in the case of the formula I, is reacted with a 1,2-diol of the formula VIII

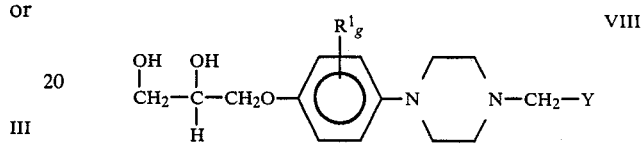

in which $R^1$, g and Y have the meanings specified in the case of the formula I, or wherein (D) a compound of the formula IX

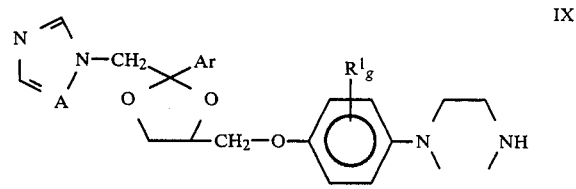

in which A, Ar, $R^1$ and g have the meanings specified in the case of the formula I, is reacted with a compound of the formula X

which E" denotes Cl, Br, I, acyloxy, such as acetyloxy or benzoyloxy, alkylsulfonyloxy, such as methanesulfonyloxy, or arylsulfonyloxy, such as benzene-, nitrobenzene- or toluenesulfonyloxy, and Y has the meanings specified under $a_1$, $a_2$, $b_1$, $b_2$, c, $d_1$, $d_2$, $d_3$, $d_4$, $d_5$, $d_6$ and $d_7$ in the case of the formula I, and the compounds of the formula I obtained by a route A)–D) are, if appropriate, converted into their physiologically acceptable acid-addition salts using inorganic or organic acids.

In this connection, the term "acyloxy" is taken to mean a straight-chain or branched $C_1$–$C_4$-alkanoyloxy radical, or a benzoyloxy radical which is unsubstituted or substituted in the phenyl nucleus by up to 2 identical or different substituents, where the substituents may denote $CH_3$, $OCH_3$, F, Cl or Br, and the term "arylsulfonyloxy" is taken to mean a phenylsulfonyloxy or naphthylsulfonyloxy radical which is unsubstituted or substituted by a Cl, Br, $CH_3$, $C_2H_5$, $OCH_3$, $OC_2H_5$ or $NO_2$, and the term "$C_1$–$C_3$-alkylsulfonyloxy" is taken to mean an n-alkanesulfonic acid radical having 1–3 carbon atoms.

For the reaction with a compound of the formula IX, any of (a) a compound of the formula $Xa_1$ or of the formula $Xa_2$

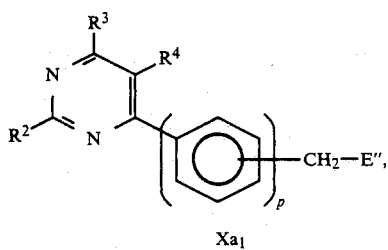

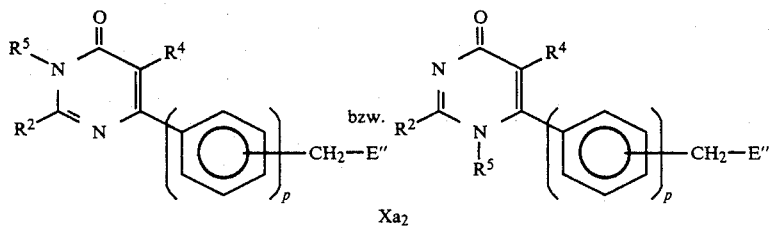

in which $R^2-R^5$ have the meanings specified in the case of formula I and E'' denotes Cl, or (b) a compound of the formula $Xb_1$ or of the formula $Xb_2$

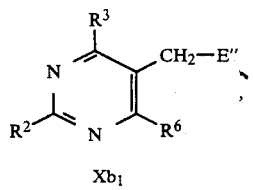

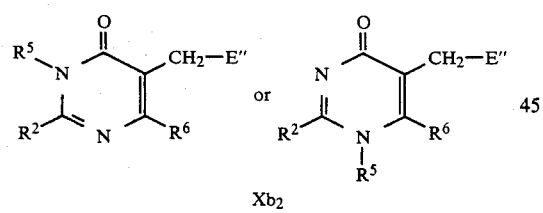

in which $R^2$, $R^3$, $R^5$ and $R^6$ have the meanings specified in the case of the formula I, and E'' denotes Br, or (c) a compound of the formula Xc,

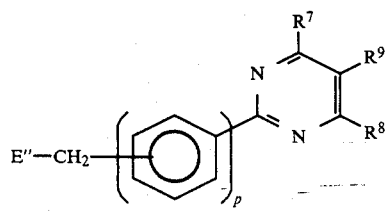

in which $R^7$, $R^8$, $R^9$ and p have the meanings specified in the case of the formula I, and E'' denotes Cl or Br, or (d) a compound of the formula $Xd_1$, of the formula $Xd_2$, of the formula $Xd_3$, of the formula $Xd_4$, of the formula $Xd_5$, of the formula $Xd_6$ or of the formula $Xd_7$,

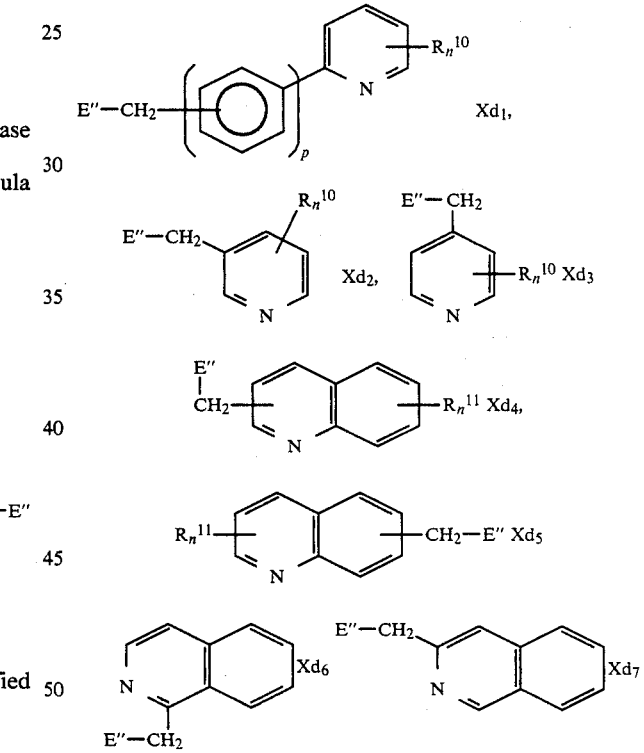

in which $R^{10}$, $R^{11}$, p and n have the meanings specified in the case of the formula I, and E'' denotes Cl or Br, are preferably used.

The process version A), where, in the case of the compounds of the formula II, E preferably denotes Cl, Br, acetoxy, trifluoroacetoxy, methanesulfonyloxy or (substituted) phenylsulfonyloxy, is carried out at a temperature between 20° C. and 160° C., advantageously between 40° C. and 120° C., in the presence of a base and expediently in an inert organic solvent, such as, for example N,N-dimethylformamide, N,N-dimethylacetamide, dimethyl sulfoxide, N-methyl-2-pyrrolidone, 1,2-dimethoxyethane, dioxane, tetrahydrofuran, 4-methyl-2-pentanone, methanol, ethanol, isopropyl alcohol, propanol, butanol, pentanol, tert.butyl alcohol, methyl glycol, methylene chloride, acetonitrile or an aromatic hydrocarbon, such as benzene, chlorobenzene, toluene or xylene. Mixtures of the solvents mentioned as examples may also be used.

Suitable bases are, for example, alkali metal or alkaline-earth metal carbonates, hydrogen carbonates, hydroxides, amides, alcoholates or hydrides, such as, for example, sodium carbonate, sodium hydrogen carbonate, potassium carbonate, sodium hydroxide, sodium amide, sodium methylate, potassium t-butylate or sodium hydride, or organic bases, for example tertiary amines, such as triethylamine, tributylamine, ethylmorpholine or pyridine, dimethylaminopyridine, quinoline or 1,5-diazabicyclo[5,4,0]undec-5-ene (DBU).

The reaction may likewise be carried out under the conditions of a phase-transfer reaction by allowing the reactants to act on one another in a suitable solvent, such as, for example, ether, dioxane, tetrahydrofuran, methylene chloride, N,N-dimethylformamide, N,N-dimethylacetamide, N-methyl-2-pyrrolidone, butanol, tert.-butanol, an aliphatic, cycloaliphatic or aromatic hydrocarbon, such as hexane, cyclohexane, benzene, toluene or xylene, methyl glycol, anisole or chlorobenzene with vigorous stirring in the presence of a phase-transfer catalyst and either a powdered alkali metal hydroxide, such as, for example, sodium hydroxide or potassium hydroxide, or a concentrated aqueous solution thereof, preferably in a temperature range from 20° C. to 120° C.

Suitable phase-transfer catalysts are, for example, trialkylbenzylammonium or tetraalkylammonium halides, hydroxides or hydrogen sulfates, preferably having 1 to 12 carbon atoms in the alkyl radical, or crown ethers, such as, for example, 12-crown-4, 15-crown-5, 18-crown-6 or dibenzo-18-crown-6.

Preparation of the starting materials:

Some of the starting compounds of the formula II, in which Ar and A have the meanings specified in the case of the formula I, are known; those which are not known may be prepared analogously to those which are known.

The process version B), where a compound of the formula IV, in which E preferably denotes Br, I, trifluoroacetyloxy, methanesulfonyloxy, benzene-, nitrobenzene-, bromobenzene- or toluenesulfonyloxy, and E' preferably denotes Cl or Br, is reacted with a compound of the formula III, in which M, $R^1$, g and Y have the specified meanings, with formation of a compound of the formula V, is carried out under the same reaction conditions as specified in the case of version A for the preparation of compounds of the formula I.

The preparation of the compounds of the formula I by reaction of compounds of the formula V with compounds of the formula VI is expediently carried out in an inert solvent in the presence of a base, such as specified in the case of the first preparation process above, preferably in a temperature range from 100° to 190° C. The reaction is expediently carried out in the presence of an alkali metal iodide, such as, for example, sodium iodide or potassium iodide, if appropriate in an autoclave under pressure.

The reactions described above may expediently be carried out as a one-pot reaction by initially reacting a compound of the formula VI with a compound of the formula III at 40° to 100° C. in the presence of a base in an inert solvent. A compound of the formula VI and, if appropriate, a further mole equivalent of a base and an alkali metal iodide (for example potassium iodide) are subsequently added, without isolation of the compound of the formula V, and the mixture is heated to 100° to 190° C.

Preparation of the starting materials:

Compounds of the formula IV, in which E and E' have the meanings specified for E in the case of the formula II, are known. They are prepared by converting a compound of the formula XI

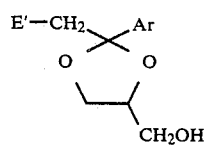

into a reactive ester group in a conventional fashion. Thus, for example, the compounds of the formula IV, in which E' preferably denotes Cl or Br, and E denotes methanesulfonyloxy, are prepared by reacting a compound of the formula XI, in which Ar has the meanings specified in the case of the formula I, and E' denotes Cl or Br, with methanesulfonyl chloride at −10° C. to +50° C., expediently in an inert solvent, in the presence of a base. Compounds of the formula IV, in which E, for example, denotes bromine, are prepared by reacting compounds of the formula XI (E'=Cl or Br) with brominating agents, such as, for example, $PBr_3$ or $POBr_3$, in an inert solvent at 0° C. to 100° C. These compounds may alternatively be prepared by reacting, by methods which are known for such ketalizations, a compound of the formula XII,

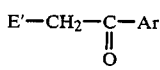

in which E' denotes Cl or Br, and Ar has the specified meanings, with 1-bromo-2,3-propanediol in an inert solvent in the presence of a strong acid with formation of a 1,3-dioxolane.

The compounds of the formula XI are known.

The process version (C), where a compound of the formula VII is reacted with a compound of the formula VIII with formation of a compound of the formula I, is generally carried out under the same conditions as for the preparation of compounds of the formula IV (version B). The ketalization of ketones of the formula VII using glycerol derivatives of the formula VIII is advantageously carried out in a mixture of solvents, comprising an inert solvent which forms an azeotropic mixture with water, such as, for example, benzene, toluene, xylene, chlorobenzene or cyclohexane, and an alcohol, in the presence of a strong acid in a temperature range from 75° to 180° C. At least 2.5 equivalents of a strong acid (relative to the azole compound of the formula VII) and, as alcohols, aliphatic alcohols having a boiling point between 75° and 150° C., and/or monoethers of lower diols, boiling between 100° and 150° C., are advantageously used in this ketalization.

Preparation of the starting materials:

The compounds of the formula VII are known and can be prepared by known methods.

Compounds of the formula VIII, in which $R^1$, g and Y have the meanings specified in the case of the formula I, are prepared by reacting compounds of the formula III with 1-halo-2,3-propanediol, in an analogous fashion to that described in Org. Synth. Collect. Vol. I, p. 296.

In the process version D), a compound of the formula IX is reacted with a heterocyclic compound of the formula X, preferably with a heterocyclic compound of the formula $Xa_1$, $Xa_2$, $Xb_1$, $Xb_2$, $Xc$, $Xd_1$, $Xd_2$, $Xd_3$, $Xd_4$, $Xd_5$, $Xd_6$ or $Xd_7$, in which $E''$ in each case has the specified meanings, expediently in an inert organic solvent in a temperature range from 20° to 180° C., preferably from 50° to 120° C. This reaction is advantageously carried out in the presence of a base, which is preferably used in an equimolar amount.

The synthesis of the compounds of the formula I from the compounds of the formulae IX and X may alternatively be carried out without adding base. The reactants of the formulae IX and X may be used in different molar ratios, i.e. either the compounds of the formula IX or the compounds of the formula X may be used in excess, but equimolar amounts are advantageously used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethylene, or mixtures of these solvents.

Suitable bases are those described as examples in the case of process version A).

The reaction may likewise be carried out under the conditions of a phase-transfer reaction, as described in the description of the process version A).

Preparation of the starting materials:

Some of the compounds of the formula IX are known; those which have meanings for Ar which differ from those known and/or in which g denotes 1 or 2 may be prepared analogously to the known compounds.

Some of the compounds of the formula X in which $E''$ and Y have the specified meanings are known. This applies particularly to compounds of the formula $Xa_1$ and $Xd_1$-$Xd_7$ where $E''=Cl$.

If the substituents $R^2$ and $R^6$-$R^{11}$ on the heterocyclic compounds $Xa_1$, $Xa_2$, $Xb_1$, $Xb_2$, $Xc$, $Xd_1$-$Xd_5$ differ from known compounds and the substituents are substantially inert, i.e. unreactive, these compounds or the precursors thereof, in which the substituents $R^2$ and $R^6$-$R^{11}$, p and n have the specified meanings, may be prepared analogously to the known compounds of these structures.

Compounds of the formula $Xa_1$ where $R^3$=hydrocarbyloxy and $R^4$=H or Br are prepared by alkylation from the corresponding, with reference to $R^2$ and $R^4$, compounds of the formula $Xa_2$ ($R^5$=H) using conventional alkylating agents, such as alkyl iodides, allyl bromide or propargyl bromide, benzyl bromide or benzyl chloride, or appropriate alkanesulfonates or arylsulfonates, such as butyl mesylate or ethyl toluenesulfonate. In this alkylation, the O-alkylated compounds of the formula $Xa_1$ where $R^3$=hydrocarbyloxy are generally produced to a predominant extent along with smaller proportions of the corresponding N-alkylated compounds of the formula $Xa_2$ where $R^5$=hydrocarbyl. This N-alkylation can occur on N-1 or N-3. In the case of the compounds according to the invention, no differentiation is made between these two structures. For this reason, two formulae are given in each case for the compounds of the formulae $Xa_2$ and $Xb_2$, and for the heterocyclic radicals Y of the structure $a_2$ and $b_2$. If compounds of the formula $Xa_2$ or $Xb_2$ are used as starting material for the preparation of compounds of the formula I in which the heterocyclic radical Y has the meaning $a_2$ or $b_2$, these are unary compounds according to the NMR spectra and TLC analysis. This means that, in the case of the compounds $Xa_2$ and $Xb_2$, $R^5$ is bonded either to N-1 or to N-3, no differentiation being made in each case, as already stated, between these two structures in the case of $a_2$ and $b_2$.

The O—alkyl compounds $Xa_1(R^3$=hydrocarbyloxy) and the N-alkyl compounds $Xa_2(R^5$=hydrocarbyl) produced together in the preparation can be separated by column chromatography on silica gel or by fractional recrystallization.

For the preparation of the N-alkylated compounds of the formulae $Xa_2$ and $Xb_2$, compounds of the formula $Xa_2$ where $R^5$=H and $E''$ preferably denotes Cl or compounds of the formula $Xb_2$ where $R^5$ and $E''$=H are alkylated using dialkyl sulfates in aqueous alkaline medium. Although, as stated above, O- and N-alkylated compounds are produced together here, the proportion of N-alkylated compounds of the formula $Xa_2$ or $Xb_2$ is greater than in the case of the alkylation using alkyl halides or sulfonates. This alkylation is preferably carried out using dimethyl sulfate, N-methylpyrimidines of the formulae $Xa_2$ or $Xb_2$ where $R^5=CH_3$ are produced to a predominant extent or virtually exclusively. The purification of these compounds, particularly the separation of O-alkyl compounds, is carried out by column chromatography or by fractional recrystallization. The following equation I serves to illustrate these syntheses.

The preparation of 5-bromomethylpyrimidines of the formulae $Xb_1$ and $Xb_2$ ($E''=Br$) is carried out starting from the appropriate 5-methylpyrimidines $Xb_1$ or $Xb_2$ ($E''=H$) by the action of N-bromosuccinimide (NBS) (cf. Equation I).

Equation I

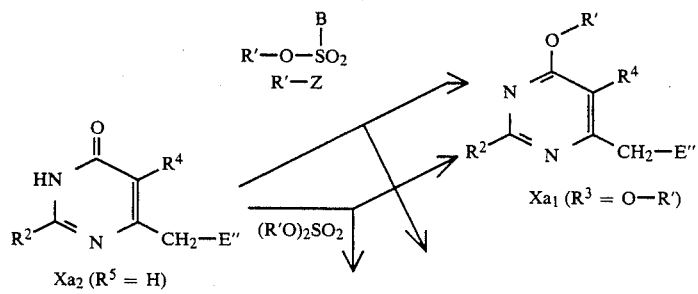

-continued
Equation I

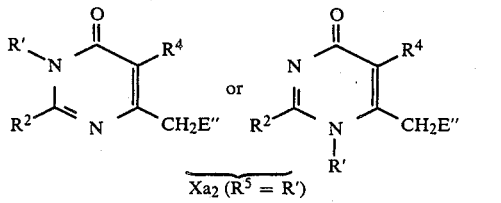

B = alkyl or aryl
Z = Cl, Br or I

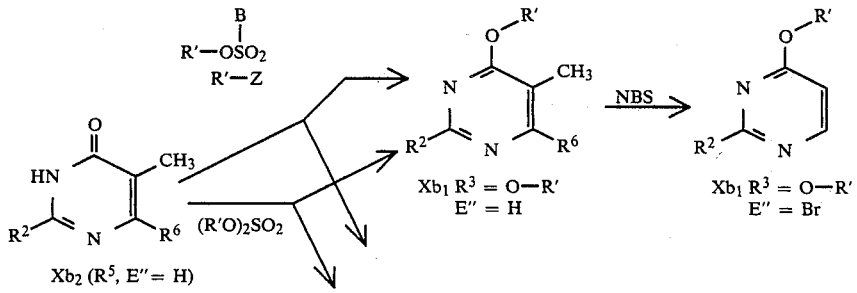

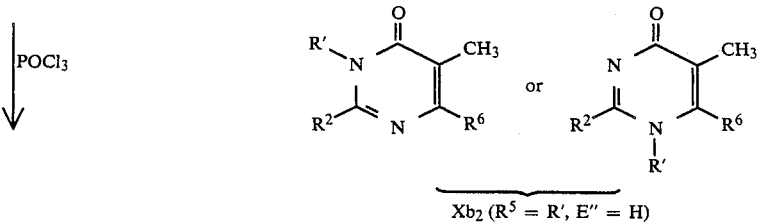

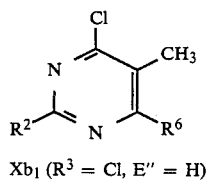

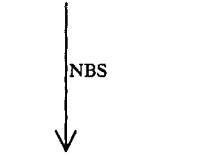

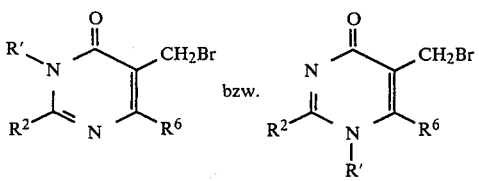

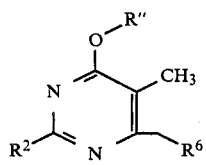

The compounds $Xa_2$ where $R^5 = H$ and $E'' = Cl$ and $Xb_2$ where $R^5$ and $E'' = H$ are known or can be prepared by known methods. Compounds of the formula $Xa_2$ where $R^4$ and $R^5 = H$ and $E'' = Cl$ can be converted into those where $R^4 = Br$, $R^5 = H$ and $E'' = Cl$ by the action of NBS.

Some compounds of the formula $Xb_1$ where $R^3 = O-R''$ and $E'' = H$, where $R''$, within the scope of the meanings specified for $R^3$ in the case of the formula I, generally denotes a hydrocarbon radical or a (substituted) phenyl radical, are known. They are prepared by converting compounds $Xb_2$ where $R^5$ and $E'' = H$, in a known fashion, by the action of phosphorus oxychloride ($POCl_3$) into the corresponding 4-chloropyrimidines of the formula $Xb_1$ where $R^3 = Cl$ and $E'' = H$, and subsequently reacting these with a compound of the formula XI (cf. Equation I). The pyrimidines $Xb_1$ where $R^3=O-R''$ and $E''=H$ thus obtained can be converted, as already stated, into the corresponding 5-bromomethylpyrimidines using NBS.

into compounds of the formula Xc where $E''=Br$ or Cl and $p=1$ by known methods, for example by bromination using NBS (cf. Equation II).

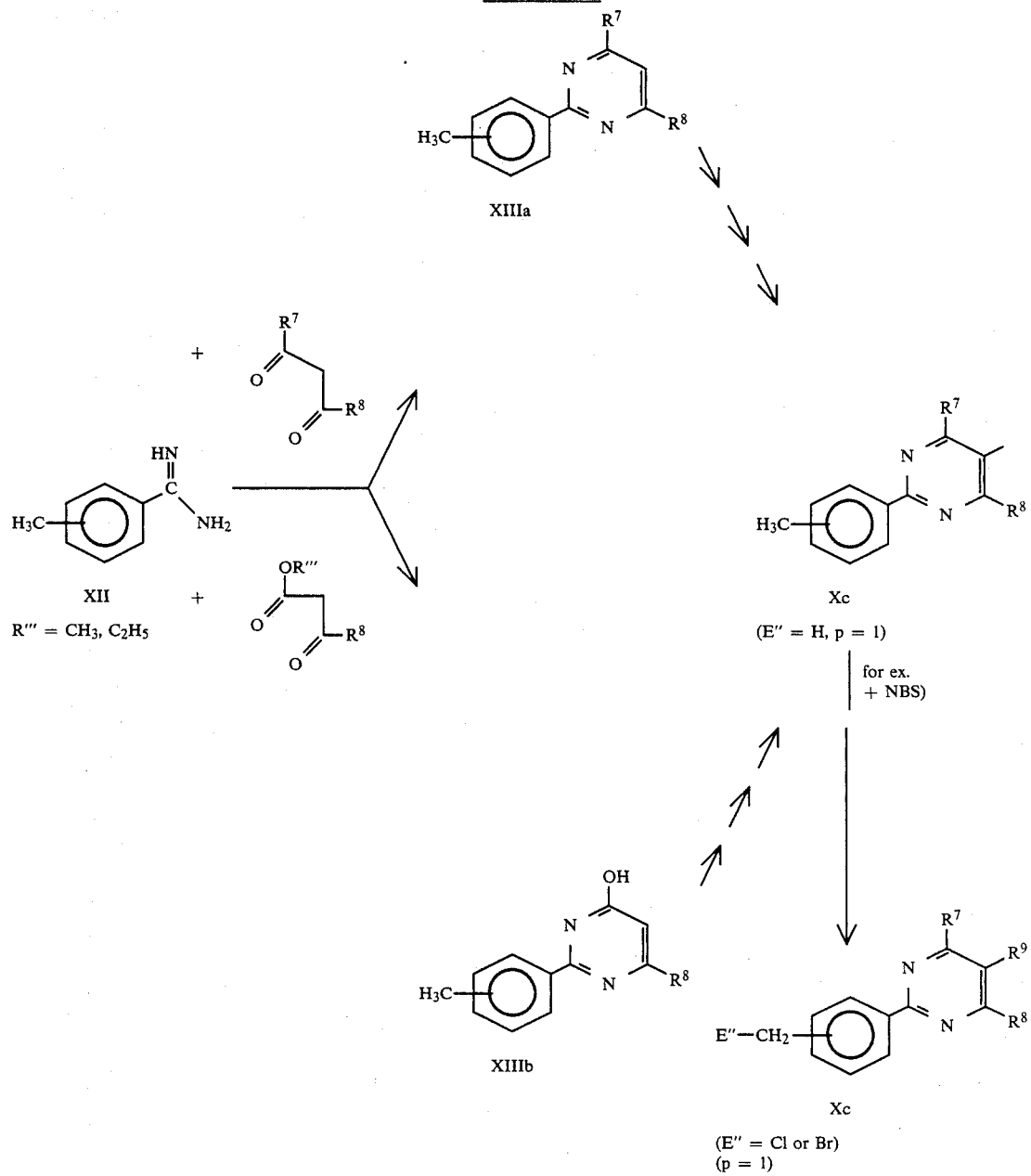

Some of the compounds Xc where $E''=Cl$ and $p=0$, are known and those in which $R^7$-$R^9$ have meanings which are different from the known compounds can be prepared analogously to those described. Compounds of the formula Xc where $p=1$ can be prepared by reacting tolylamidines of the formula XII, or the salts thereof, with correspondingly structured 1,3-diketones or 3-keto esters by known methods, with formation of 2-tolylpyrimidines of the formulae XIIIa or XIIIb, and converting these by known methods into the pyrimidine derivative of the formula Xc, in which $R^7$, $R^8$ and $R^9$ have the specified meanings and $E''$denotes H, required in each case (cf. Equation II). Those 2-(tolyl)-pyrimidines of the formula Xc where $E''=H$ can be converted The compounds of the formulae $Xd_1$, $Xd_2$, $Xd_3$, $Xd_4$ and $Xd_5$ in which $E''$ denotes Cl or Br, p denotes 0 and n denotes 0, 1 or 2 are known, and those in which $R^{10}$ or $R^{11}$ has a meaning which differs from the compounds described can be prepared analogously to the known compounds. Compounds of the formula $Xd_1$ where $E''=H$ and $p=1$ are known. They are converted into those in which $E''$ denotes Cl or Br, for example by the action of NBS or by other known halogenation methods.

The compounds of the formulae $Xd_1$-$Xd_5$ in which $E''$ denotes OH and p denotes 0 and $R^{10}$, n and $R^{11}$ have the specified meanings are known and can be converted into corresponding compounds of the formulae $Xd_1-Xd_5$ where E''=Cl by known methods, for example by the action of thionyl chloride.

The compounds of the formula $Xd_4$ in which E'' denotes H, n denotes 1 or 2 and $R^{11}$ denotes Cl or $OCH_3$ can be prepared by the methods which are known for the synthesis of quinolines.

The compounds of the formula $Xd_5$ where E''=H thus obtained are converted into corresponding bromomethylquinolines of the formula $Xd_5$ (E''=Br) in which $R^{11}$ and n have the specified meanings and n preferably denotes 1 by the action of NBS (cf. Equation III below).

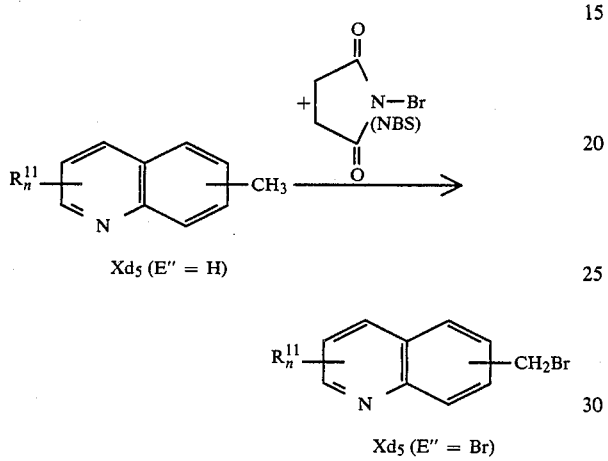

Depending on the process version and depending on the temperature range, the reaction times are a few minutes to several hours.

If necessary, the process products can be purified by recrystallization from a suitable solvent or mixture of solvents or by column chromatography on silica gel.

The diastereomeric racemates (cis or trans form) of the compounds of the formula I can be separated in a conventional fashion, for example by selective, fractional crystallization or column chromatography.

Since the stereochemical configuration is already specified in the intermediates of the formula II, the separation into the cis and trans form can be carried out as early as this stage, or even earlier, for example at the stage of the intermediates of the general formula IV, or in the case of the intermediates of the formula IX.

The cis and trans diastereomeric racemates can themselves be separated in a conventional fashion into their optical antipodes cis(+), cis(−) or trans(+) and trans(−).

The process versions A, B and D are preferably used for the preparation of compounds of the formula I.

The invention furthermore relates to compounds of the formula IIIa,

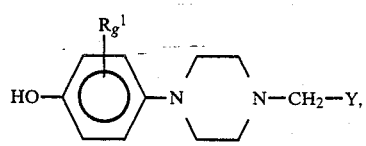

in which:
$R^1$ denotes $C_1-C_3$-alkyl, F or Cl,
g denotes 0, 1 or 2, and

Y denotes one of the following heterocyclic radicals

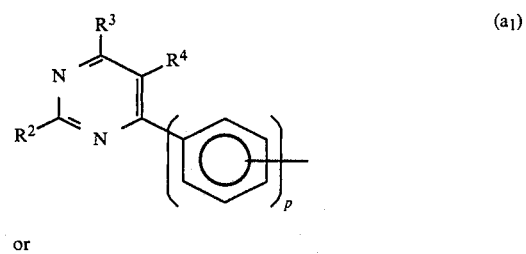

(a₁)

or

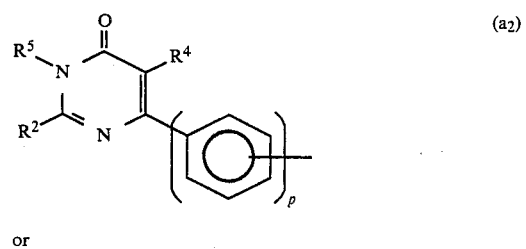

(a₂)

or

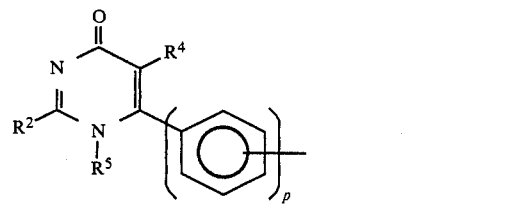

or

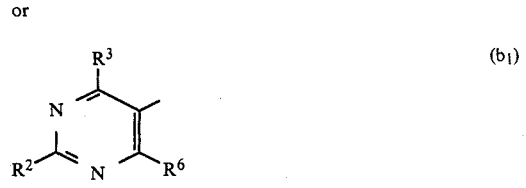

(b₁)

or

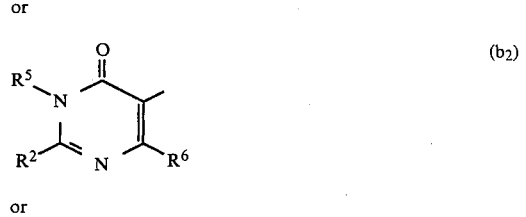

(b₂)

or

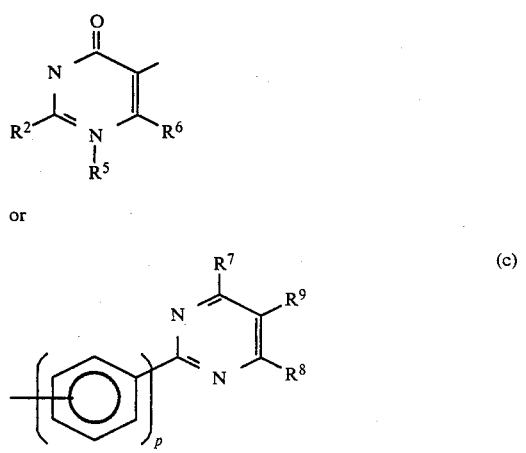

(c)

in which $R^2$ denotes H, $C_1$-$C_8$-alkyl, $C_1$-$C_4$-alkoxy, a phenyl group which is unsubstituted or carries 1 or 2 substituents, where the substituents may be identical or different and denote F, Cl, Br, I, trifluoromethyl, methoxy, ethoxy, nitro or $C_1$-$C_4$-alkyl, or a phenyl-$C_1$-$C_2$-alkyl group which is unsubstituted or carries 1 or 2 substituents in the phenyl radical, where the substituents may be identical or different and denote F, Cl, Br, $OCH_3$, $OC_2H_5$, $CH_3$ or $C_2H_5$, or, in the case of the heterocyclic radicals $a_1$ and $a_2$, if p denotes zero, additionally denotes $C_1$-$C_4$-alkylthio or a benzylthio group which is unsubstituted or carries 1 or 2 substituents in the phenyl radical, where the substituents may be identical or different and denote F, Cl, $OCH_3$, $OC_2H_5$, $CH_3$ or $C_2H_5$, $R^3$ denotes H, OH, Cl, $C_1$-$C_4$-alkoxy or a benzyloxy group which is unsubstituted or carries 1 or 2 substituents in the phenyl radical, where the substituents may be identical or different and denote F, Cl, Br, $OCH_3$, $OC_2H_5$, $CH_3$ or $C_2H_5$, and, in the case of the heterocyclic radical $b_1$, additionally denotes $C_1$-$C_4$-alkyl or a phenyloxy group which is unsubstituted or carries 1 or 2 substituents, where the substituents may be identical or different and denote F, Cl, Br, $OCH_3$, $OC_2H_5$, $CH_3$ or $C_2H_5$, $R^4$ denotes H, Cl, Br or CN, denotes H, $C_1$-$C_4$-alkyl, prop-2-en-1-yl, prop-1-in-1-yl or benzyl, denotes 0 or 1, the phenylene radical in $a_1$, $a_2$ and c being bonded via the 2, 3 or 4 position, denotes H, $C_1$-$C_8$-alkyl, ($C_3$-$C_6$-cycloalkyl)-$C_1$-$C_3$-alkyl, a phenyl group which is unsubstituted or carries 1 or 2 substituents, where the substituents may be identical or different and denote F, Cl, Br, I, $OCH_3$, $OC_2H_5$, 1,2—O—$CH_2$—O—, $CF_3$ or $C_1$-$C_4$-alkyl, a phenyl-$C_1$-$C_2$-alkyl group which is unsubstituted or substituted in the phenyl radical by $OCH_3$, $OC_2H_5$, 1,2—O-$CH_2$-O-, $CF_3$, F, Cl or $C_1$-$C_4$-alkyl, or $CF_3$, $R^7$ and $R^8$, independently of one another, denote H, $C_1$-$C_8$-alkyl, $C_1$-$C_4$-alkoxy, or a phenyl or benzyl group which is unsubstituted or carries 1 or 2 substituents in the phenyl radical, where the substituents may be identical or different and denote F, Cl, Br, $OCH_3$ or $OC_2H_5$, and where, in addition, $R^7$ may alternatively denote OH, and $R^9$ denotes H, Cl, Br or CN, or Y denotes one of the following heterocyclic radicals

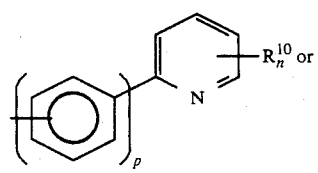 (d₁)

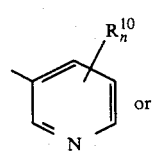 (d₂)

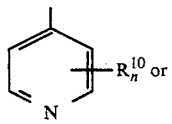 (d₃)

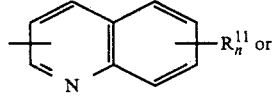 (d₄)

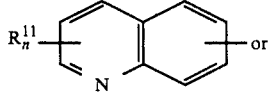 (d₅)

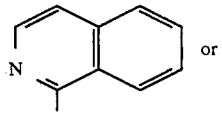 (d₆)

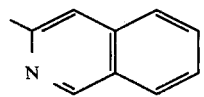 (d₇)

in which

P denotes 0 or 1, $R^{10}$ denotes Cl, Br, $OCH_3$, $OC_2H_5$, $CH_3$ or $C_2H_5$, n denotes 0, 1 or 2, $R^{10}$ being in the 3, 4, 5 and/or 6 position in $d_1$, in the 2, 4, 5 and/or 6 position in $d_2$, and in the 2, 3, 5 and/or 6 position in $d_3$, and $R^{11}$ denotes Cl, $OCH_3$, $CH_3$ or $C_2H_5$, and is in one or two of the free positions in $d_4$ and $d_5$, and the heterocyclic radical $d_4$ is bonded via the 2, 3 or 4 position, and the heterocyclic radical $d_5$ is bonded via the 5, 6, 7 or 8 position, and the phenylene unit in the radical $d_1$ is bonded via the 2, 3 or 4 (para) position, and the acid-addition salts thereof.

Preferred compounds of the formula IIIa are those in which at least one of the substituents or indices $R^1$, g, Y, $R^2$-$R^{11}$, p and n has the following meanings:

$R^1$ denotes $CH_3$ or $C_2H_5$, g denotes 0 or 2, and where Y denotes a heterocyclic radical $a_1$, $a_2$, $b_1$, $b_2$ or C:

$R^2$ denotes H, $C_1$-$C_4$-alkyl, $CH_3O$, or a phenyl or benzyl group which is unsubstituted or carries 1 or 2 substituents in the phenyl radical, where the substituents may be identical or different and denote F, Cl, Br or $OCH_3$, $R^3$ denotes H or $C_1$-$C_4$-alkoxy, and, in the case of the radical $b_1$, additionally denotes a phenyloxy gooup which is unsubstituted or carries 1 or 2 substituents, where the substituents may be identical or different and denote F, Cl, Br, $OCH_3$ or $OC_2H_5$, $R^4$ denotes H or CN, $R^5$ denotes $CH_3$, p denotes 0 or 1, $R^6$ denotes H, $C_1$-$C_8$-alkyl, ($C_5$-$C_6$-cycloalkyl)-$C_1$-$C_2$-alkyl, a phenyl group which is unsubstituted or carries 1 or 2 substituents, where the substituents may be identical or different and denote F, Cl, Br, $OCH_3$, $OC_2H_5$ or $CF_3$, a benzyl group which is unsubstituted or substituted in the phenyl radical by OCH₃, CF₃, F or Cl, or CF₃, R⁷ and R⁸, independently of one another, denote C₁–C₈-alkyl, C₁–C₄-alkoxy, or a phenyl or benzyl group which is unsubstituted or substituted in the phenyl radical by F, Cl, OCH₃ or OC₂H₅, and, in addition, R⁷ alternatively denotes H or OH, and R⁹ denotes H or CN, or when Y denotes a heterocyclic radical d₁, d₂, d₃, d₄, d₅, d₆ or d₇: p1 denotes 0 or 1, R¹⁰ denotes Cl, CH₃ or C₂H₅, n denotes 0 or 1, where R¹⁰ in d₃ is preferably in the 2 position, and R¹¹ denotes Cl, the phenylene unit in the radical d₁ preferably being bonded via the 4 position.

Particularly preferred compounds of the formula IIIa are those in which at least one of the substituents or indices has the following meanings:

R¹ denotes CH₃, g denotes 0 or 2, and, where Y denotes a heterocyclic radical a₁, a₂, b₁, b₂ or c:

R² denotes a phenyl or benzyl group which is unsubstituted or carries 1 or 2 substituents in the phenyl radical, where the substituents may be identical or different and denote F, Cl or OCH₃, and, in the case of the radical b₁, additionally denote C₁–C₄-alkyl, R³ denotes H, and, in the case of the radical b₁, additionally denotes a phenyloxy group which is unsubstituted or substituted by F, Cl, OCH₃ or OC₂H₅, R⁴ denotes H, R⁵ denotes CH₃, p denotes 0 or 1 in the heterocyclic radicals a₁ and a₂ and denotes 1 in the heterocyclic radical c, R⁶ denotes C₁–C₈-alkyl, (C₅–C₆-cycloalkyl)-C₁–C₂-alkyl, a phenyl group which is unsubstituted or substituted by F, Cl, OCH₃ or OC₂H₅, a benzyl group which is unsubstituted or substituted in the phenyl radical by F, Cl or OCH₃, or CF₃, R⁷ and R⁸, independently of one another, denote C₁–C₃-alkyl, or a phenyl or benzyl group which unsubstituted or substituted in the phenyl radical by F, Cl or OCH₃, and, in addition, R⁷ alternatively denotes H or C₁–C₄-alkoxy, and R⁹ denotes H, or where Y denotes a heterocyclic radical d₁, d₂, d₃, d₄, d₅, d₆ and d₇:

p denotes 1, and n denotes 0, the radical d₄ preferably being bonded via the 2 position and the radical d₅ preferably being bonded via the 6 or 7 position.

The compounds of the formula IIIa, in which R¹, g and Y have the specified meanings are new and represent valuable intermediates for the preparation of the compounds of the formula I which have a strong antimycotic or fungicidal action. Some of the compounds of the formula IIIa likewise have an antimycotic or fungicidal action. Some of the compounds of the formula IIIa additionally exhibit pharmacological actions, such as, for example, actions on the cardiovascular system.

In addition, the invention relates to a process for the preparation of compounds of the formula IIIa, wherein a compound of the formula XIV,

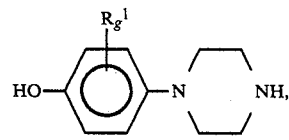  XIV in which R¹ and g have the meanings specified in the case of the formula I, or a salt of this compound, is reacted with a compound of the formula X,

E''—CH₂—Y    X, in which

E'' denotes Cl, Br, I, acyloxy, such as acetoxy or benzoyloxy, alkylsulfonyloxy, such as methane-sulfonyloxy, or arylsulfonyloxy, such as benzene-, nitrobenzene- or toluenesulfonyloxy, and has the meanings specified under a₁, a₂, b₁, b₂, c, d₁, d₂, d₃, d₄, d₅, d₆ and d₇ in the case of the formula I, and, if appropriate, the compounds of the formula IIIa obtained are converted into their acid-addition salts using inorganic or organic acids.

For the reaction according to the invention with compounds of the formula XIV, any of (a) a compound of the formula Xa₁ or of the formula Xa₂,

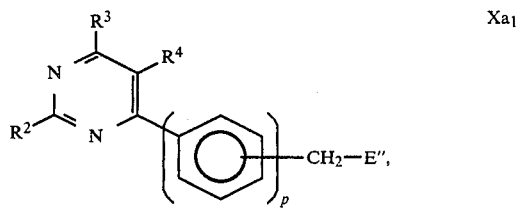

in which R²–R⁵ have the meanings specified in the case of the formula I, and E'' denotes Cl or Br, or (b) a compound of the formula Xb₁ or of the formula Xb₂

-continued

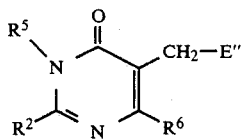
bzw

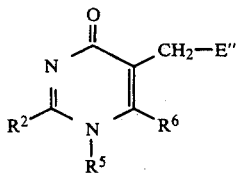
Xb₂ in which R², R³, R⁵ and R⁶ have the meanings specified in the case of the formula I, and E" denotes Br, or (c) a compound of the formula Xc,

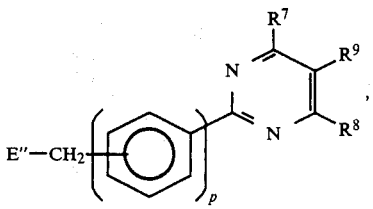
Xc in which R⁷, R⁸, R⁹ and p have the meanings specified in the case of the formula I, and E" denotes Cl or Br, or (d) a compound of the formula Xd₁, of the formula Xd₂, of the formula Xd₃, of the formula Xd₄, of the formula Xd₅, of the formula Xd₆ or of the formula Xd₇

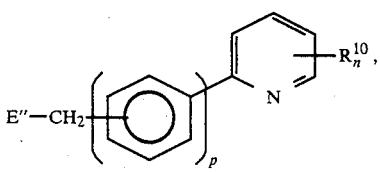
Xd₁

Xd₂

Xd₃

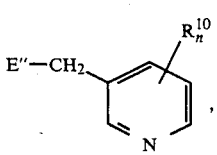

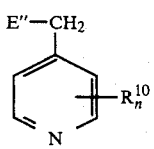

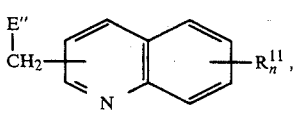
Xd₄

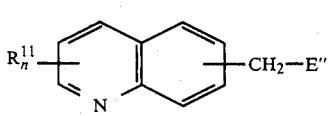
Xd₅

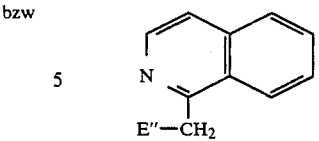
Xd₆

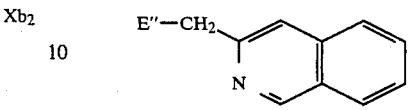
Xd₇ in which R¹⁰, R¹¹, p and n have the meanings specified in the case of the formula I, and E" denotes Cl or Br, are preferably used.

The process, according to the invention, for the preparation of compounds of the formula IIIa is expediently carried out in an inert organic solvent in a temperature range from 20° to 180° C., preferably from 50° to 120° C., advantageously in the presence of a base, which is preferably used in an equivalent amount. If salts of the compounds of the formula XIV are used for the process, the stoichiometric amount of base corresponding to the amount of salt is added. If desired, a further proportion of base can then be used in addition. The synthesis of compounds of the formula IIIa from the compounds of the formulae XIV and X can also be carried out without the addition of base if the compounds XIV are not used as the salt. The reactants of the formulae XIV and X can be used in different molar ratios, i.e. in each case either the compounds of the formula XIV or those of the formula X can be used in excess, but equimolar amounts are advantageously used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethylene, or mixtures of these solvents.

Suitable bases are those mentioned as examples in the process version A).

Depending on the temperature range, the reaction times are a few minutes to several hours.

If necessary, the process products can be purified by recrystallization from a suitable solvent or mixture of solvents or by column chromatography on silica gel.

Preparation of the starting materials:

The compound of the formula XIV where g=0 is known. The compounds of the formula XIV in which g denotes 1 or 2 and R¹ has the meaning specified in the case of the formula I are prepared, analogously to the known compounds, by reaction of appropriate 4-methoxyanilines with bis-(2-chloroethyl)amine and subsequent cleavage of the phenol ether using concentrated aqueous hydrobromic acid. The preparation of the compounds of the formula X in which E" and Y have the specified meanings, if they are not known, has already been described in process version D) for the preparation of compounds of the formula I.

The compounds of the formula I and their acid-addition salts are valuable medicaments. They have an antimicrobial action and in particular are suitable for the prevention and treatment of fungal infections in humans and in various types of mammal.

In vitro, the new compounds have a very good action against dermatophytes, such as, for example, *Trichophy-* ton mentagrophytes, Microsporum canis and Epidermophyton floccosum; against mold fungi, such as, for example, Aspergillus niger, or against yeasts, such as, for example, Candida albicans, C. tropicalis, Torulopsis glabrata and Trichosporon cutaneum, or against protozoa, such as Trichomonas vaginalis or T. fetus, or against Gram-positive and Gram-negative bacteria.

After oral or parenteral administration, the compounds also have a very good systemic effect in vivo, for example against Candida albicans, for example in experimental kidney candidiasis of the mouse. There is likewise a very good effect against various pathogens of dermatomycosis (for example Trichophyton mentagrophytes) in guinea pigs after oral, parenteral or, local administration, The following may be mentioned as examples of areas of indication in human medicine:

Dermatomycosis and systemic mycosis caused by Tricho-phyton mentagroohytes and other Trichophyton species, Microsporon species, Epidermophyton floccosum, gemmiparous fungi, biphasic fungi and mold fungi.

The following may be mentioned as examples of areas of indication in veterinary medicine:

All dermatomycoses and systemic mycoses, particularly those which are caused by the abovementioned pathogens.

The present invention includes pharmaceutical preparations, which, beside nontoxic, inert pharmaceutically suitable excipients, contain one or more active compounds according to the invention or which comprise one or more active compounds according to the invention, and also processes for the preparation of these preparations.

Nontoxic, inert pharmaceutically suitable excipients are taken to mean solid, semisolid or liquid diluents, fillers and formulation auxiliaries of all types.

Suitable forms of administration are, for example, tablets, dragees, capsules, pills, aqueous solutions, suspensions, and emulsions, optionally sterile injectable solutions, nonaqueous emulsions, suspensions and solutions, ointments, creams, pastes, lotions, sprays etc.

The therapeutically active compounds should preferably be present in the abovementioned pharmaceutical preparations in a concentration from about 0.01 to 99.0, preferably from about 0.05 to 50% by weight of the total mixture.

The abovementioned pharmaceutical preparations may also contain further pharmaceutical active compounds in addition to the active compounds according to the invention.

The abovementioned pharmaceutical preparations are prepared in a conventional fashion by known methods, for example by mixing the active compound(s) with the excipient(s).

The present invention also includes the use of the active compounds according to the invention and the use of pharmaceutical preparations which contain one or more active compounds according to the invention, in human and veterinary medicine for the prevention, improvement and or cure of the abovementioned disorders.

The active compounds or the pharmaceutical preparations may be administered locally, orally, parenterally, intraperitoneally and/or rectally.

In order to achieve the desired results, it has generally proven expedient, both in human and in veterinary medicine, to administer the active compound or compounds according to the invention in total amounts of about 0.05, preferably 0.1, in particular 0.5 mg and at most 200, preferably 100, in particular 30 mg/kg of bodyweight per 24 hours, if appropriate in the form of several individual doses. The total amount is administered in 1 to 8, preferably in 1 to 3, individual doses.

However, it may be necessary to deviate from the dosages mentioned, and in particular to do so as a function of the species and the bodyweight of the object to be treated, the nature and severity of the disorder, the type of the preparation and the administration of the medicament, and the period of time or interval over which the administration is effected. Thus, it may in some cases be sufficient to manage with less than the abovementioned amount of active compound, whereas in other cases, it is necessary to exceed the abovementioned amount of active compound. The optimum dosage and the type of administration of the active compounds required in each case can easily be determined by any expert, on the basis of his expert knowledge.

The new compounds of the formula I are also suitable for the treatment of protozoosis in humans and animals as is caused, for example, by infection by Trichomonas vaginalis, Entamoeba histolytica, Trypanosoma cruzi and Leishmania donovani.

The new compounds may be administered orally or locally. Oral administration is carried out in pharmaceutically conventional preparations, for example in the form of tablets or capsules.

The compounds of the formula I are also active as biocides. They are distinguished, in particular, by their fungicidal activity in the case of phytopathogenic fungi. Even the fungal pathogens which have already penetrated into the vegetative tissue can be combated successfully. This is particularly important and advantageous in those fungal diseases which, once the infection has occurred, cannot be combated effectively using the fungicides which are otherwise conventional. The range of action of the new compounds covers a large number of different phytopathogenic fungi, such as, for example, Piricularic oryzae, Plasmopara viticola, Various types of rust, but above all Venturia inaequalis, Cercospora beticola and true mildew fungi in fruit, vegetable, cereal and ornamental plant growing.

The new compounds of the formula I are furthermore suitable for use in industrial areas, for example as wood-protection agents, as preservatives in paints, in cooling lubricants for metal working, or as preservatives in drilling and cutting oils.

The new compounds may be used in the conventional preparations as wettable powders, emulsifiable concentrates, sprayable solutions, dusting agents, dressing agents, dispersions, granules or microgranules.

The following examples serve to illustrate the invention in greater detail, without limiting it.

Examples of the preparation process version (A)

EXAMPLE 1

0.184 g (6.13 mmol) of 80% strength sodium hydride/oil dispersion were added to a solution of 2.26 g (6 mmol) of 4-(4-(4-hydroxyphenyl)piperazin-1-ylmethyl)-6-methoxy-2-phenylpyrimidine in 20 ml of absolute N,N-dimethylformamide (DMF). After the evolution of hydrogen had subsided, a solution of 2.49 g (6.1 mmol) of 2-S(R)-(2,4-dichlorophenyl)-2-(1,2,4-triazol-1-ylmethyl)-4-R,(S)-methanesulfonyloxymethyl-1,3-dioxolane(cis form) in 16 ml of absolute DMF was added at room temperature, and the mixture was stirred for 4 hours at 100° C. The DMF was subsequently removed by distillation in vacuo (3-10 mbar) in a rotary evaporator, 50 ml of water and 50 ml of CH₂Cl₂ were added to the residue, the mixture was shaken thoroughly, the phases were separated, and the aqueous phase was extracted a further three times with CH₂Cl₂. The combined CH₂Cl₂ extracts were dried using MgSO₄, filtered and evaporated in vacuo. The residue (5.5 g) was dissolved in 12 ml of methanol, whereupon the crystalline precipitate was produced. This was isolated (3.02 g) and recrystallized from a 2:3 mixture of CH₃CN and CH₂Cl₂ by evaporating off the major part of the CH₂Cl₂ at atmospheric pressure after dissolving at the boiling point. On cooling, pure 2-S,(R)-(2,4-dichlorophenyl)-2-(1,2,4-triazol-1-ylmethyl)-4-R,(S)-[4-(4-(4-methoxy-2-phenylpyrimidin-6-ylmethyl)-piperazin-1-yl)phenoxymethyl]-1,3-dioxolane (cis form) crystallized out. After filtering off under suction, washing with CH₃CN and drying, 2.75 g (66.6% yield) of this compound were obtained; melting point 146-47° C., elemental analysis: $C_{35}H_{35}Cl_2N_7O_4$ (MW 688.64) calc. C 61.05, H 5.12, Cl 10.30, N 14.24; found C 60.8, H 5.2, Cl 10.3, N 14.3%; the ¹H NMR spectrum (CDCl₃) confirms the structure.

EXAMPLE 2

The compounds of the formula I (Ar: 2,4-dichlorophenyl, cis form) listed in Table 1 below were prepared according to Example 1, in each case using the methanesulfonates IIb or IIc (cf. Table 1) and the appropriate compounds of the formula IIIa (cf. Table 1).

TABLE 1

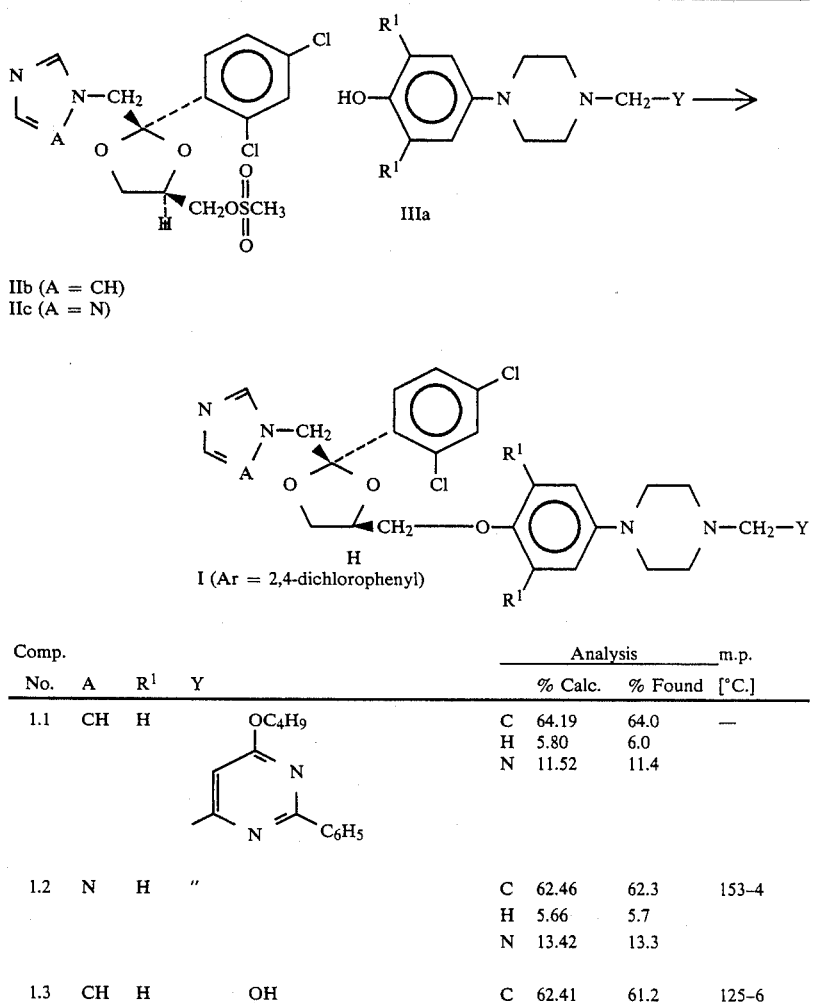

IIb (A = CH)
IIc (A = N)

I (Ar = 2,4-dichlorophenyl)

| Comp. No. | A | R¹ | Y | % Calc. | % Found | m.p. [°C.] |
|---|---|---|---|---|---|---|
| 1.1 | CH | H | OC₄H₉ / pyrimidine-C₆H₅ | C 64.19 H 5.80 N 11.52 | 64.0 6.0 11.4 | — |
| 1.2 | N | H | " | C 62.46 H 5.66 N 13.42 | 62.3 5.7 13.3 | 153-4 |
| 1.3 | CH | H | OH / pyrimidine-C₆H₅ | C 62.41 H 5.09 N 12.48 | 61.2 4.9 12.0 | 125-6 |
| 1.4 | N | H | " | C 60.53 H 4.93 N 14.55 | 60.3 4.9 14.1 | 163-4 |

TABLE 1-continued

| No. | | | Structure | | Analysis | | m.p. |
|---|---|---|---|---|---|---|---|
| 1.5 | CH | H | 4-chlorophenyl-6-methyl-4-hydroxypyrimidine | C<br>H<br>N | 59.37<br>4.70<br>11.87 | 58.9<br>4.6<br>11.6 | 153–4 |
| 1.6 | CH | H | N-methyl-2-phenyl pyrimidinone derivative | C<br>H<br>N | 62.88<br>5.28<br>12.22 | 62.3<br>5.3<br>12.0 | 154–5 |
| 1.7 | N | H | " | C<br>H<br>N | 61.05<br>5.12<br>14.24 | 60.5<br>5.2<br>14.0 | 151–2 |
| 1.8 | CH | H | 2-ethyl-4-(4-methylphenyl)pyrimidine | C<br>H<br>N | 64.81<br>5.59<br>12.26 | 64.1<br>5.7<br>11.6 | — |
| 1.9 | CH | CH$_3$ | 4-methoxy-6-methyl-2-phenylpyrimidine | C<br>H<br>N | 63.77<br>5.63<br>11.74 | 63.4<br>5.5<br>11.6 | — |
| 1.10 | CH | H | 4,5,6-trimethyl-2-phenylpyrimidine | C<br>H<br>N | 64.81<br>5.59<br>12.26 | 64.6<br>5.6<br>12.3 | 134–35 |
| 1.11 | CH | H | 4-(4-chlorophenyl)-2,5,6-trimethylpyrimidine | C<br>H<br>N | 61.71<br>5.18<br>11.67 | 61.2<br>5.3<br>11.3 | — |
| 1.12 | CH | H | 4-methoxy-2-methyl-6-(4-methylphenyl)pyrimidine | C<br>H<br>N | 63.34<br>5.46<br>11.98 | 62.8<br>5.3<br>11.4 | — |
| 1.13 | CH | CH$_3$ | 2-methyl-4-(4-methylphenyl)pyrimidine | C<br>H<br>N | 65.23<br>5.76<br>12.01 | 64.5<br>5.8<br>12.1 | — |

EXAMPLE 3

0.58 g (5.15 mmol) of potassium tert.-butylate was added to a solution of 1.73 g (5 mmol) of 4-(4-hydroxyphenyl)-1-(4-(2-pyridyl)benzyl)piperazine in 20 ml of absolute DMF at room temperature, the mixture was stirred for 8 minutes, a solution of 2.04 g (5 mmol) of IIb (cf. Example 2, Table 1) in 15 ml of absolute 1,2-dimethoxyethane (DME) was then added, and the mixture was stirred for 5 hours at 91°–92° C. The solvent was subsequently stripped off in vacuo, the residue was taken up in water/CH$_2$Cl$_2$, and the phases were separated after thorough mixing. The aqueous phase was extracted a further twice with CH$_2$Cl$_2$. The combined CH$_2$Cl$_2$ extracts were dried, filtered and evaporated. The residue remaining (2.9 g) crystallized from methanol. After filtering off under suction, washing with ice-cold methanol and drying, 2.31 g ($\triangleq$ 70.4% yield) of pure cis-2-(2,4-dichlorophenyl)-2-(imidazol-1-ylmethyl)-4-[4-(4-(4-(2-pyridyl)benzyl)piperazin-1-yl)phenoxymethyl]-1,3-dioxolane were obtained, melting point 89°–90° C.; analysis: C$_{36}$H$_{35}$Cl$_2$N$_5$O$_3$ (MW 656.63) calc. C 65.85 H 5.37 N 10.67; found C 65.7 H 5.3 N 10.5.

EXAMPLE 4

According to the same procedure as described in Example 3, likewise on a 5 mmol scale, using the same piperazine derivative as intermediate and using IIb (cf. Example 2, Table 1) and using 0.203 g (5.2 mmol) of sodium amide as base in place of potassium tert.-butylate, otherwise under the same reaction conditions as described in Example 3, 2.19 g (66.8% yield) of cis-2-(2,4-dichlorophenyl)-2-(imidazol-1-ylmethyl)-4-[4-(4-(4-(2-pyridyl)benzyl)-piperazin-1-yl)phenoxymethyl]-1,3-dioxolane, melting point 88°–90° C., were obtained.

EXAMPLE 5

0.145 g (4.83 mmol) of 80% strength NaH-oil dispersion was added to a solution of 1.79 g (4.7 mmol) of 5-(4-(4-hydroxyphenyl)piperazin-1-ylmethyl)-2-(4-chlorophenyl)pyrimidine in 19 ml of absolute DMF at room temperature. When the evolution of hydrogen had subsided, a solution of 1.974 g (4.85 mmol) of IIb (cf. Example 2, Table 1) in 15 ml of absolute DMF was added at room temperature, and the mixture was subsequently stirred for 2 hours at 102°–104° C. The mixture was then worked up as described in Example 1. The CH$_2$Cl$_2$ extract residue (3.02 g) crystallized from methanol. After filtering off under suction, washing with methanol and drying, 2.73 g (84% yield) of pure 2-S,(R)-(2,4-dichlorophenyl)-2-(imidazol-1-ylmethyl)-4--R,(S)-[4-(4-(2-(4-chlorophenyl)pyrimidin-5-ylmethyl)-piperazin-1-yl)phenoxymethyl]-1,3-dioxolane (cis form) were obtained; melting point 153–54° C., analysis: C$_{35}$H$_{33}$Cl$_3$N$_6$O$_3$ (MW 692.07) calc. C 6074, H 4.81, N 12.14; found C 60.5, H 4.6, N 12.1%; the $^1$H NMR spectrum (CDCl$_3$) confirms the structure.

Dimethyl sulfoxide, N,N-dimethylacetamide or N-methyl-2-pyrrolidone, and also mixtures of these solvents with, for example, tetrahydrofuran, dioxane, 1,2-dimethoxyethane or acetonitrile may be used in place of dimethylformamide using principally the same procedure as described above.

EXAMPLE 6

The compounds of the formula I (Ar: 2,4-dichlorophenyl, cis form) listed in Table 2 below were prepared according to Example 5, in each case using the methanesulfonates IIb or IIc (cf. Table 1) and the appropriate compounds of the formula IIIb (Y, cf. Table 2).

If the compounds of the formula I were not to be purified after work-up by crystallization or recrystallization, the CH$_2$Cl$_2$ extract residue was in each case chromatographed on a silica gel S (Riedel-de Haen, particle size 0.063–0.2 mm)/CH$_2$Cl$_2$ column. Fractions were eluted with CH$_2$Cl$_2$ and further with CH$_2$Cl$_2$/C$_2$H$_5$OH mixtures of a successively increasing C$_2$H$_5$OH content (up to a maximum of 5% by volume of C$_2$H$_5$OH), and the fractions were investigated by thin-layer chromatography (TLC) (prepared TLC plates, silica gel 60, F 254, Merck). The compounds indicated in Table 2 by (*) were obtained in pure form in this fashion by column chromatography.

TABLE 2

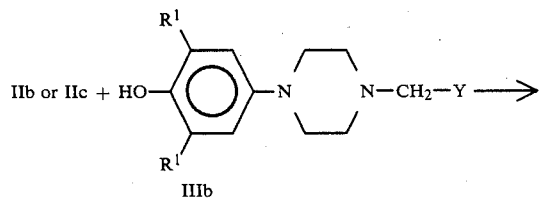

TABLE 2-continued
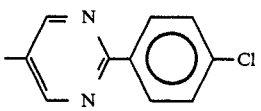
| Comp. No. | A | R¹ | Y | Analysis % Calc. | % Found | m.p. [°C.] |
|---|---|---|---|---|---|---|
| 2.2 | N | H | " | C 62.01<br>H 5.05<br>Cl 10.77 | 61.8<br>5.0<br>10.8 | 118-9 |
| 2.3 | N | H | 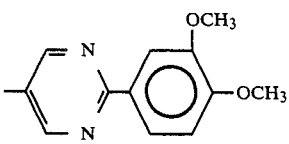 | C 58.92<br>H 4.65<br>N 14.15 | 58.5<br>4.7<br>14.1 | 79-80 |
| 2.4* | N | H | 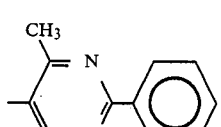 | C 60.17<br>H 5.19<br>N 13.64 | 59.9<br>5.2<br>13.3 | — |
| 2.5 | CH | H | 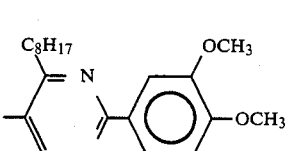 | C 64.38<br>H 5.40<br>N 12.51 | 64.3<br>5.3<br>12.5 | 160-1 |
| 2.6 | N | H | " | C 62.50<br>H 5.25<br>N 14.58 | 62.4<br>5.2<br>14.2 | 154-5 |
| 2.7* | CH | H | 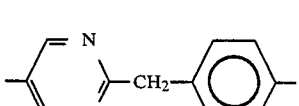 | C 65.13<br>H 6.56<br>N 10.13 | 64.3<br>6.4<br>10.1 | — |
| 2.8* | CH | CH₃ | 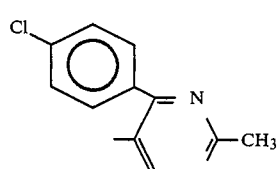 | C 62.17<br>H 5.35<br>N 11.45 | 61.7<br>5.2<br>11.2 | — |
| 2.9 | CH | H |  | C 61.24<br>H 5.00<br>N 11.90 | 59.7<br>5.2<br>11.5 | 120-21 |

TABLE 2-continued
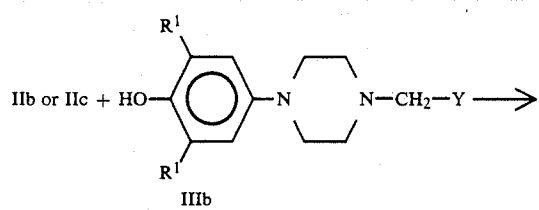
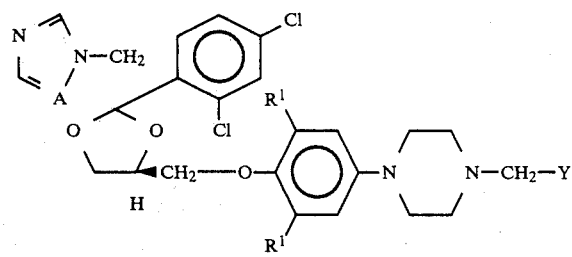
IIIb  Ia (Ar = 2,4-dichlorophenyl)
| Comp. No. | A | R¹ | Y | Analysis % Calc. | % Found | m.p. [°C.] |
|---|---|---|---|---|---|---|
| 2.10* | CH | H | ![C3H7 group with N, phenyl, N-CH3, O] | C 64.19<br>H 5.80<br>N 11.52 | 64.1<br>5.6<br>11.2 | — |
| 2.11* | N | H | " | C 62.47<br>H 5.64<br>N 13.42 | 62.0<br>5.4<br>13.0 | — |
| 2.12* | CH | CH₃ | ![OCH3, N, phenyl, N, C3H7] | C 64.99<br>H 6.12<br>N 11.09 | 64.4<br>6.0<br>10.8 | — |
| 2.13 | CH | CH₃ | ![H3C, N, phenyl, N] | C 65.23<br>H 5.76<br>N 12.01 | 64.8<br>5.8<br>11.6 | — |
| 2.14 | CH | H | ![phenyl-pyrimidine] | C 63.92<br>H 5.21<br>N 12.78 | 63.5<br>5.0<br>12.4 | — |
| 2.15* | CH | H | ![2,4,6-trimethylpyrimidine CH3, N, N, CH3] | C 61.08<br>H 5.62<br>N 13.77 | 60.1<br>5.3<br>13.3 | — |

TABLE 2-continued

IIb or IIc + IIIb ⟶

IIIb   Ia (Ar = 2,4-dichlorophenyl)

| Comp. No. | A | R¹ | Y | Analysis % Calc. | | % Found | m.p. [°C.] |
|---|---|---|---|---|---|---|---|
| 2.16* | CH | H | phenyl-pyrimidine with CH₃ | C | 64.38 | 64.1 | — |
|  |  |  |  | H | 5.40 | 5.5 |  |
|  |  |  |  | N | 12.51 | 12.1 |  |
| 2.17* | CH | H | 4,6-dimethyl-2-phenyl-pyrimidine | C | 64.81 | 65.0 | — |
|  |  |  |  | H | 5.59 | 5.5 |  |
|  |  |  |  | N | 12.26 | 12.1 |  |
| 2.18 | N | H | " | C | 62.97 | 62.7 | 149–50 |
|  |  |  |  | H | 5.43 | 5.2 |  |
|  |  |  |  | N | 14.28 | 14.2 |  |
| 2.19* | CH | H | 4-methyl-6-isopropoxy-2-phenyl-pyrimidine | C | 64.19 | 64.0 | — |
|  |  |  |  | H | 5.80 | 5.8 |  |
|  |  |  |  | N | 11.52 | 11.5 |  |
| 2.20 | N | H | 2-(pyridin-2-yl)phenyl | C | 63.92 | 63.8 | 126–27 |
|  |  |  |  | H | 5.21 | 5.2 |  |
|  |  |  |  | N | 12.78 | 12.8 |  |
| 2.21 | CH | H | pyridin-2-yl | C | 62.07 | 61.3 | 133–34 |
|  |  |  |  | H | 5.38 | 5.4 |  |
|  |  |  |  | N | 12.06 | 11.7 |  |
| 2.22 | N | H | " | C | 59.90 | 59.5 | 129–30 |
|  |  |  |  | H | 5.20 | 5.3 |  |
|  |  |  |  | N | 14.45 | 14.1 |  |
| 2.23 | N | H | pyridin-3-yl | C | 59.90 | 59.8 | 106–07° |
|  |  |  |  | H | 5.20 | 5.3 |  |
|  |  |  |  | N | 14.45 | 14.4 |  |

TABLE 2-continued

IIb or IIc + HO-[phenyl with R¹ groups]-N(piperazine)N-CH₂-Y →

[Structure IIIb reacts to give Ia (Ar = 2,4-dichlorophenyl)]

| Comp. No. | A | R¹ | Y | Analysis % Calc. | % Found | m.p. [°C.] |
|---|---|---|---|---|---|---|
| 2.24 | CH | CH₃ | 3-pyridyl | C 63.15<br>H 5.80<br>N 11.51 | 63.0<br>5.8<br>11.4 | — |
| 2.25 | CH | H | 4-pyridyl | C 62.07<br>H 5.38<br>N 12.06 | 62.2<br>5.1<br>11.8 | |
| 2.26 | N | CH₃ | 4-pyridyl | C 61.08<br>H 5.62<br>N 13.79 | 60.4<br>5.5<br>13.5 | 112–13 |
| 2.27 | CH | H | 3-methoxy-6-methyl-2-pyridyl | C 61.54<br>H 5.65<br>N 11.35 | 61.1<br>5.3<br>11.0 | 138–39 |
| 2.28 | CH | H | quinolin-2-yl | C 64.76<br>H 5.28<br>N 11.11 | 64.0<br>5.3<br>10.6 | — |
| 2.29 | N | H | " | C 62.76<br>H 5.11<br>N 13.31 | 61.9<br>5.1<br>13.0 | 160–61 |
| 2.30 | CH | H | 6-methylquinolin-2-yl | C 64.76<br>H 5.28<br>N 11.11 | 64.1<br>5.2<br>10.5 | — |

TABLE 2-continued

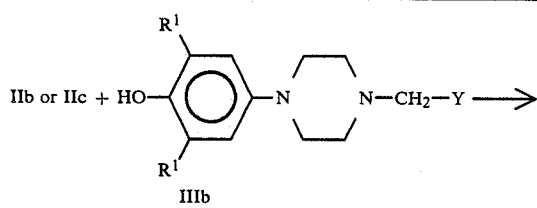

IIIb

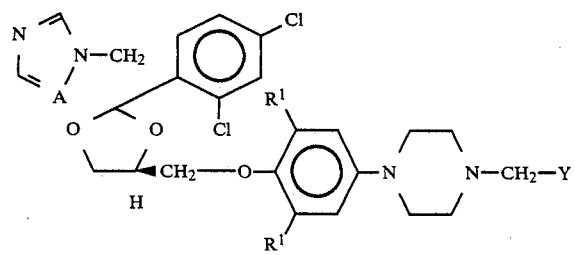

IIIb    Ia (Ar = 2,4-dichlorophenyl)

| Comp. No. | A | R¹ | Y | | Analysis % Calc. | % Found | m.p. [°C.] |
|---|---|---|---|---|---|---|---|
| 2.31 | CH | H | ![structure with C3H7, N, phenyl, N, O, phenyl-OCH3] | C<br>H<br>N | 65.77<br>5.64<br>10.23 | 65.1<br>5.4<br>9.8 | — |

EXAMPLE 7

A mixture of 1.37 g (3.8 mmol) of 4-(4-hydroxyphenyl)-1-(4-(4-methylpyrimidin-2-yl)benzyl)piperazine, 35 ml of toluene, 5.5 ml of 50% strength sodium hydroxide solution, 1.55 g (3.8 mmol) of IIb (cf. Table 1) and 0.29 g of tetrabutylammonium bromide was stirred vigorously for 3 hours at 100° C. The phases were then separated, and the concentrated sodium hydroxide solution washed twice with ether. The combined organic phases were washed twice with water, dried, filtered and evaporated in vacuo. The extract residue (2.35 g) was chromatographed as described in Example 6 on a silica gel S (Riedel-de Haen, particle size 0.063–0.2 mm)/CH$_2$Cl$_2$ column (diameter 2.1 cm, height 28 cm). The pure fractions, unary according to TLC, were mixed and evaporated in vacuo. 2.17 g(≙ 85.1% yield) of pure cis-2-(2,4-dichlorophenyl)-2-(imidazol-1-ylmethyl)-4-[4-(4-(4-(4-methylpyrimidin-2-yl)-benzyl)piperazin-1-yl)phenoxymethyl]-1,3-dioxolane were obtained as a highly viscous oil; analysis: C$_{36}$H$_{36}$Cl$_2$N$_6$O$_3$ (MW 671.65) calc. C 64.38, H 5.40, Cl 10.56, N 12.51; found C 64.2, H 5.5, Cl 10.7, N 12.3%.

EXAMPLE 8

The compounds of the formula I (g=0 or 2, R¹ denotes H or CH$_3$ in the 2,6 position) listed in Table 3 were prepared by the same procedure as described in Example 7 starting from IIb or IIc (cf. Table 1) and in each case the appropriate compound IIIb (Y, cf. Table 3).

TABLE 3
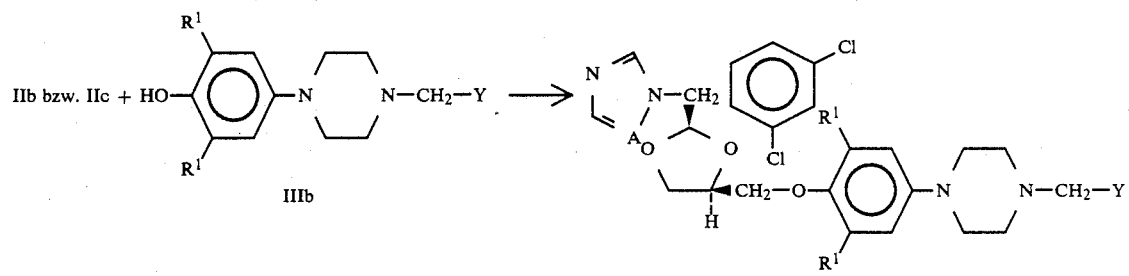
| Comp. No. | A | R¹ | Y | | Analysis % Calc. | Found |
|---|---|---|---|---|---|---|
| 3.1 | CH | H | pyrimidine-CH₃ | C H N | 60.50 5.42 14.11 | 60.1 5.3 14.0 |
| 3.2 | N | CH₃ | pyrimidine-C₃H₇ | C H N | 60.73 6.02 15.02 | 60.5 6.0 14.8 |
| 3.3 | CH | CH₃ | 2-phenyl-4-C₃H₇-pyrimidine | C H N | 66.02 6.09 11.55 | 66.2 5.9 11.1 |
| 3.4 | CH | CH₃ | 4-(CH₂CH₂-cyclopentyl)-2-CH₃-pyrimidine | C H N | 65.08 6.72 11.68 | 64.7 6.6 11.8 |
| 3.5 | N | CH₃ | 2-(4-methylphenyl)-4,6-diCH₃-pyrimidine | C H N | 63.36 5.78 13.72 | 63.7 5.8 13.5 |
| 3.6 | CH | H | 2-phenyl-4-C(CH₃)₃-5-CN-pyrimidine | C H N | 66.29 5.70 11.60 | 66.0 5.7 11.4 |
| 3.7 | CH | H | 2-CH₃-5-CN-4-phenyl-pyrimidine | C H N | 63.79 5.06 14.08 | 63.4 4.9 13.7 |
| 3.8 | N | H | 2,6-diCH₃-pyridine | C H N | 60.50 5.42 14.11 | 60.1 5.3 14.2 |

TABLE 3-continued

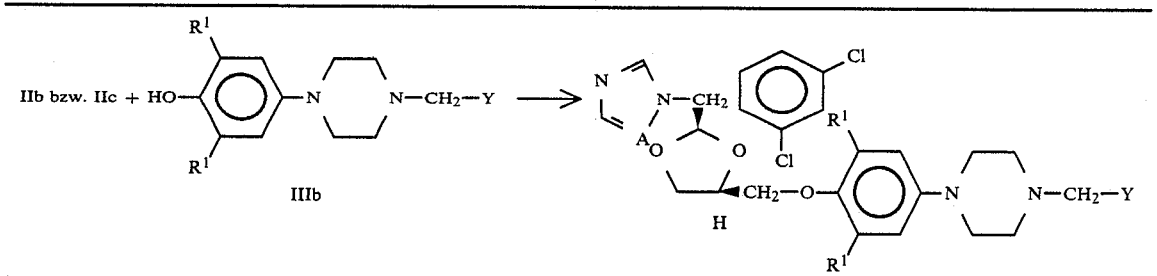

| Comp. No. | A | R¹ | Y | | Analysis % Calc. | Found |
|---|---|---|---|---|---|---|
| 3.9 | CH | H | (3-pyridyl) | C | 62.07 | 61.5 |
| | | | | H | 5.38 | 5.3 |
| | | | | N | 12.06 | 11.6 |
| 3.10 | N | CH$_3$ | (2-methylquinolinyl) | C | 65.11 | 64.8 |
| | | | | H | 5.62 | 5.4 |
| | | | | N | 10.85 | 10.8 |
| 3.11 | CH | H | (6-methylquinolinyl) | C | 64.76 | 64.0 |
| | | | | H | 5.28 | 5.1 |
| | | | | N | 11.11 | 10.7 |
| 3.12 | CH | CH$_3$ | " | C | 65.65 | 65.3 |
| | | | | H | 5.66 | 5.5 |
| | | | | N | 10.63 | 10.3 |

EXAMPLE 9 (Salt formation)

0.29 ml of a 6M solution of HCl in ether was added to a solution of 580 mg (0.864 mmol) of 2-S,(R)-(2,4-dichlorophenyl)-2-(imidazol-1-ylmethyl)-4-R,(S)-[4-(4-(4-methyl-2-phenylpyrimidin-5-ylmethyl)piperazin-1-yl)phenoxymethyl]-1,3-dioxolane (cis form) (cf. Example 6, No. 2.5) in 20 ml of CH$_2$Cl$_2$, whereupon a crystalline precipitate was produced. The mixture was evaporated in vacuo, the crystalline residue remaining was boiled with 10 ml of ethyl acetate and, after cooling to about 7° C., filtered off under suction and dried. 620 mg ($\dotplus$96% yield of the dihydrochloride) of cis-2-(2,4-dichlorophenyl)-2-(imidazol-1-ylmethyl)-4-[4-(4-(4-methyl-2-phenylpyrimidin-5-ylmethyl)piperazin-1-yl)phenoxymethyl]-1,3-dioxolane dihydrochloride were obtained, melting point 180°-81° C., analysis: C$_{36}$H$_{38}$Cl$_4$N$_6$O$_3$ (MW 744.58), calc. Cl (total) 19.04, Cl$^\ominus$9.52, found Cl (total) 18.8, Cl$^\ominus$9.6%.

EXAMPLES OF THE PREPARATION PROCESS VERSION (B)

EXAMPLE 10

(a) 0.60 g of 80% strength sodium hydride/oil dispersion was added to a solution of 7.21 g (20 mmol) of 5-(4-(4-hydroxyphenyl)piperazin-1-ylmethyl)-4-methyl-2-phenylpyrimidine in 70 ml of absolute N,N-dimethylformamide (DMF) at room temperature (with cooling). When the evolution of hydrogen was complete, a solution of 8.40 g (20 mmol) of cis-2-bromomethyl-2-(2,4-dichlorophenyl)-4-methanesulfonyloxymethyl-1,3-dioxolane (cis and trans relate to the bromomethyl and methanesulfonyloxymethyl group in the 2 and 4 positions respectively of the dioxolane ring) in 25 ml of absolute DMF was added dropwise at room temperature, and the mixture was stirred for 8 hours at 60°-63° C. The subsequent work-up and column chromatography was carried out in the same fashion as described in Examples 1 and 6. The chromatographic purification was carried out on silica gel S/CH$_2$Cl$_2$/petroleum ether 3:1 column (diameter 3.6 cm, height 37 cm) with elution using CH$_2$Cl$_2$/petroleum ether 3:1, CH$_2$Cl$_2$ and CH$_2$Cl$_2$/C$_2$H$_5$OH mixtures (increasing C$_2$H$_5$OH content, to a maximum of 3% by volume). 8.76 g (64.0% of theory) of cis-2-bromomethyl-2-(2,4-dichlorophenyl)-4-[4-(4-(4-methyl-2-phenylpyrimidin-5-ylmethyl)piperazin-1-yl)phenoxymethyl]-1,3-dioxolane were obtained as a highly viscous oil, analysis: C$_{33}$H$_{33}$BrCl$_2$N$_4$O$_3$ (684.49) calc. C 57.91, H 4.86, Br 11.68, Cl 10.36, N 8.19; found C 57.3, H 4.6, Br 11.9, Cl 10.0, N 7.8%.

(b) 0.375 g (12.5 mmol) of 80% strength NaH/oil dispersion was added to a solution of 0.85 g (12.5 mmol) of imidazole in 25 ml of absolute N,N-dimethylacetamide. When the evolution of hydrogen was complete, a solution of 6.85 g (10 mmol) of the bromomethyl compound prepared under a) in 10 ml of absolute N,N-dimethylacetamide was added dropwise, and the mixture was subsequently refluxed for 24 hours. The mixture was then worked up as described in Example 1.

The dimethylacetamide was removed by distillation in an oil-pump vacuum on a rotary evaporator. The CH$_2$Cl$_2$ extract residue (6.8 g) was chromatographed as described in Example 6 on a silica gel S/CH$_2$Cl$_2$ column (diameter 2.6 cm, height 40 cm). 2.55 g of a highly-concentrated substance which crystallized from methanol producing 2.18 g ($\dotplus$5% yield) of pure cis-2-(2,4-dichlorophenyl)-2-(imidazol-1-ylmethyl)-4-[4-(4-(4-methyl-2-phenylpyrimidin-5-ylmethyl) piperazin-1- yl)phenoxymethyl]-1,3-dioxolane were obtained in this fashion melting point 160°-61° C.; analysis: found C 64.2, H 5.3, N 12.3% (calculated values cf. Example 6, No. 2.5).

EXAMPLE 11

Using the same procedure as was described in Example 10a, starting from 15.5 mmol of 4-(4-hydroxyphenyl)-1-(4-(4-methylpyrimidin-2-yl)benzyl)piperazine, the appropriate amount of NaH and 15.5 mmol of cis-2-bromomethyl-2-(2,4-dichlorophenyl)-4-methanesulfonyloxymethyl-1,3-dioxolane, 6.92 g ($\hat{=}$65.2% of theory) of cis-2-bromomethyl-2-(2,4-dichlorophenyl)-4-[4-(4-(4-(4-methylpyrimidin-2-yl)benzyl)-piperazin-1-yl)phenoxymethyl]-1,3-dioxolane were obtained as a viscous oil; analysis: $C_{33}H_{33}BrCl_2N_4O_3$ (684.49) calc. C 57.91, H 4.86, Br 11.68, Cl 10.36, N 8.19; found C 56.8, H 4.6, Br 12.0, Cl 10.2, N 7.7%.

EXAMPLE 12

A solution of 1.023 g (14.83 mmol) of 1,2,4-triazole in 6 ml of absolute dimethyl sulfoxide (DMSO) was added dropwise to a suspension of 0.49 g (16.3 mmol) of 80% strength NaH/oil dispersion in 15 ml of absolute DMSO at room temperature, the mixture was stirred for a further 30 minutes at room temperature, a solution of 6.85 g (10 mmol) of cis-2-bromomethyl-2-(2,4-dichlorophenyl)-4-[4-(4-(4-(4-methylpyrimidin-2-yl)benzyl)piperazin-1-yl)phenoxmethyl]-1,3-dioxolane, prepared according to Example 11, in 7 ml of absolute DMSO was subsequently added dropwise, and the mixture was stirred for 20 hours at 130° C. under a nitrogen atmosphere. After cooling, the reaction mixture was stirred into 120 ml of water. This mixture was extracted repeatedly with $CH_2Cl_2$. The combined $CH_2Cl_2$ extracts were dried, filtered and evaporated in vacuo. The residue (7.1 g) was purified as described in Example 6 by chromatography on a silica gel S/$CH_2Cl_2$ column (diameter 2.6 cm, height 42 cm). 2.43 g ($\hat{=}$36.2% yield) of virtually pure cis-2-(2,4-dichlorophenyl)-2-(1,2,4-triazol-1-ylmethyl)-4-[4-(4-(4-(4-methylpyrimidin-2-yl)benzyl)piperazin-1-yl)phenoxymethyl]-1,3-dioxolane, melting point 126°-27° C., were obtained from the fractions which were unary according to TLC; analysis: $C_{35}H_{35}Cl_2N_7O_3$ (672.64) calc. C 62.50, H 5.25, N 14.58; found C 62.5, H 5.2, N 14.2%.

EXAMPLE 13

(a) A mixture of 2.16 g (6 mmol) of 4-(4-hydroxyphenyl)-1-(4-methyl-2-phenylpyrimidin-5-ylmethyl)-piperazine, 60 ml of toluene, 2.22 g (6 mmol) of cis-2-bromomethyl-2-(4-fluorophenyl)-4-methanesulfonyloxymethyl-1,3-dioxolane, 0.40 g of tetrabutylammonium bromide and 8 ml of 50% strength sodium hydroxide solution were stirred vigorously for 3.75 hours at 56° C. The phases were subsequently separaed at room temperature, the sodium hydroxide solution was extracted by shaking three times with ether, and the toluene and ether phases were combined. These were extracted by shaking three times with water, dried, filtered and evaporated in vacuo. The residue remaining (5.0 g) was chromatographed on a silica gel S/$CH_2Cl_2$ column (diameter 2.1 cm, height 30 cm) with elution using $CH_2Cl_2$ and $CH_2Cl_2/C_2H_5OH$ mixtures (100:0.25–100:1 v/v). After elution of a preliminary fraction (0.45 g), the fractions which were unary accord-ing to TLC were combined and evaporated in vacuo. 3.40 g (=89.5% yield) of cis-2-bromomethyl-2-(4-fluorophenyl)-4-[4-(4-(4-methyl-2-phenylpyrimidin-5-ylmethyl)piperazin-1-yl)phenoxymethyl]-1,3-dioxolane were obtained as a highly viscous oil ("cis" relates to the 2-bromomethyl group and the phenoxymethyl group in the "4 position"); analysis: $C_{33}H_{34}BrFN_4O_3$ (Mw 633.58) cal 62.56, H 5.41, Br 12.61, 12.61, F 3.00, N 8.84; found C 62.1, H 5.3, Br 15.0, F 2.9, N 8.8%.

(b) As described in Example 10b, 3.40 g (5.36 mmol) of cis-2-bromomethyl-2-(4-fluorophenyl)-4-[4-(4-(4-methyl-2-phenylpyrimidin-5-ylmethyl)piperazin-1-yl)phenoxymethyl]-1,3-dioxolane were reacted with 0.714 g (10.5 mmol) of imidazole and 0.315 g (10.5 mmol) of 80% strength NaH/oil dispersion in 33 ml of absolute N,N-dimethylacetamide. After refluxing for 30 hours, the dimethylacetamide was removed by distillation in an oil-pump vacuum on a rotary evaporator. The residue was taken up in $CH_2Cl_2$/water.

After separation of the phases, the aqueous phase was extracted repeatedly with $CH_2Cl_2$. The combined $CH_2Cl_2$ extracts were shaken with water, dried, filtered and evaporated in vacuo. The residue (3.96 g) was chromatographed on a silica gel S/$CH_2Cl_2$ column (diameter 2.1 cm, height 34 cm) with elution using $CH_2Cl_2$ and $CH_2Cl_2/C_2H_5OH$ mixtures (with increasing $C_2H_5OH$ content, to a maximum of 5% by volume of $C_2H_5OH$). After elution of 2.5 g of 2-bromomethyldioxolane starting compound, the fractions which were unary according to TLC were combined and evaporated in vacuo. This produced, as residue, 0.51 g of virtually pure cis-2-(4-fluorophenyl)-2-(imidazol-1-ylmethyl)-4-[4-(4-(4-methyl-2-phenylpyrimidin-5-ylmethyl)-piperazin-1-yl)phenoxymethyl]-1,3-dioxolane (yield$\hat{=}$15.3%), analysis: $C_{36}H_{37}FN_6O_3$ (MW 620.74) calc. C 69.66, H 6.01, F 3.06, N 13.54; found C 68.6, H 6.0, F 2.9, N 13.2%.

EXAMPLE 14

A mixture of 3.77 g (14 mmol) of 4-(4-hydroxyphenyl)-1(pyrid-2-ylmethyl)piperazine, 200 ml of toluene, 5.88 g (14 mmol) of 2-bromomethyl-2-(2,4-dichlorophenyl)-4-methanesulfonyloxymethyl-1,3-dioxolane, 0.80 g of tetrabutylammonium bromide and 27 ml of 50% strength sodium hydroxide solution was stirred vigorously for 3 hours at 65° C. The phases were subsequently separated at room temperature. The toluene solution was shaken three times with water, dried, filtered and evaporated in vacuo. The residue remaining (8.8 g) was chromatographed on a silica gel S/$CH_2Cl_2$ column (diameter 2.6 cm, height 28.0 cm) with elution using $CH_2Cl_2$ and $CH_2Cl_2/C_{25}OH$ mixtures (to a maximum $C_2H_5OH$ content of 4% by volume). After elution of a preliminary fraction (1.45 g), the fractions which were unary according to TLC were combined and evaporated in vacuo. 6.02 g ($\hat{=}$72.4% yield) of 2-bromomethyl-2-(2,4-dichlorophenyl)-4-[4-(4-(pyrid-2-ylmethyl)piperazin-1-yl)phenoxymethyl]-1,3-dioxolane (cis/trans mixture) were obtained as a highly viscous oil, analysis: $C_{27}H_{28}BrCl_2N_3O_3$ (MW 593.38) calc. C 54.65, H 4.76, Br 13.47, Cl 11.95, N 7.08; found C 53.5, H 4.9, Br 13.1, Cl 13.2, N 6.5%.

EXAMPLE 15

4.75 g (8 mmol) of 2-bromomethyl-2-(2,4-dichlorophenyl)-4-[4-(4-(pyrid-2-ylmethyl)piperazin-1-yl)phenoxymethyl]-1,3-dioxolane were reacted as described in Example 10b with 0.68 g (10 mmol) of imidazole and 0.30 g (10 mmol) of 80% strength NaH/oil dispersion in 28 ml of absolute N,N-dimethylacetamide with formation of 1.53 g (≈33% of theory) of 2-(2,4-dichlorophenyl)-2-(imidazol-1-ylmethyl)-4-[4-(4-(pyrid-2-ylmethyl)piperazin-1-yl)phenoxymethyl]-1,3-dioxolane; melting point 134°–135° C., analysis: found C 61.7, H 5.2, N 12.0% (calculated values, cf. Example 6, No. 2.21).

EXAMPLES OF THE PREPARATION PROCESS VERSION (D)

EXAMPLE 16

A solution of 2.45 g (5 mmol) of 2-S,(R)-(2,4-dichlorophenyl)-2-(imidazol-1-ylmethyl)-4-R,(S)-(4-piperazinophenoxymethyl)-1,3-dioxolane (cis form) and 1.87 g (5 mmol) of 2-(4-bromomethyl-1-phenyl)-4,6-dimethylpyrimidine in 20 ml of absolute DMF was warmed to 80° C. with protection against atmospheric moisture, and 115 mg of powdered potassium carbonate were added after 10 minutes with stirring. A further 115 mg of powdered $K_2CO_3$ were added after a further 25 minutes, and a 3rd portion of 115 mg of just such $K_2CO_3$ was added after a further 60 minutes (in total 345 mg (2.5 mmol) of $K_2CO_3$). The mixture was subsequently stirred for a further 3 hours at 80° C., the DMF was removed by distillation in an oil-pump vacuum in a rotary evaporator, and the residue was taken up in 30 ml of water and 100 ml of $CH_2Cl_2$. After separation of the phases, the aqueous phase was extracted a further twice with $CH_2Cl_2$. The combined $CH_2Cl_2$ extracts were dried, filtered and evaporated in vacuo. The residue (3.72 g) was purified as described in Example 6 by column chromatography on a silica gel $S/CH_2Cl_2$. 2.71 g (79% of theory) of pure cis-2-(2,4-dichlorophenyl)-2-(imidazol-1-ylmethyl)-4-[4-(4-(4-(4,6-dimethylpyrimidin-2-yl)benzyl)piperazin-1-yl)phenoxymethyl]-1,3-dioxolane were obtained as a viscous oil; analysis: found C 64.6, H 5.5, N 12.0% (cf. Example 6, No. 2.17).

EXAMPLE 17

The compounds of the formula I listed in Table 4 were prepared by process version D) by the same procedure as described in Example 16, starting from IXa or IXb (cf. Table 4) and in each case the appropriate compound of the formula Xa.

TABLE 4

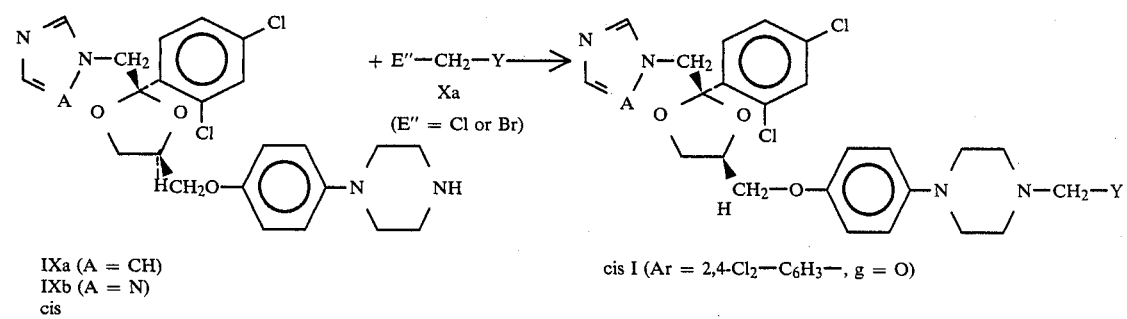

IXa (A = CH)
IXb (A = N)
cis cis I (Ar = 2,4-$Cl_2$—$C_6H_3$—, g = O)

| Comp. No. | A | Y | Analysis | % Calc. | % Found | m.p. [°C.] |
|---|---|---|---|---|---|---|
| 4.1 | CH | ![pyrimidine with OC2H5, CH2-phenyl-OCH3, OCH3] | C<br>H<br>N | 61.93<br>5.72<br>10.83 | 61.0<br>5.6<br>10.3 | 129–30 |
| 4.2 | N | ![phenyl-pyrimidine-CH3] | C<br>H<br>N | 62.50<br>5.25<br>14.58 | 62.4<br>5.3<br>14.2 | — |
| 4.3 | CH | ![phenyl-pyrimidine OCH3/CH3] | C<br>H<br>N | 63.34<br>5.46<br>11.98 | 62.0<br>5.4<br>11.4 | — |
| 4.4 | CH | ![pyrimidine-phenyl-Cl] | C<br>H<br>N | 60.74<br>4.81<br>12.14 | 60.5<br>4.7<br>11.9 | 153–54 |

TABLE 4-continued
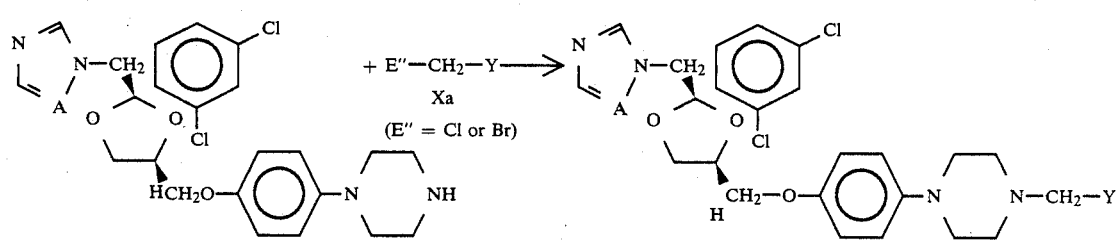
IXa (A = CH)
IXb (A = N)
cis
cis I (Ar = 2,4-Cl$_2$—C$_6$H$_3$—, g = O)
| Comp. No. | A | Y | | Analysis | | m.p. [°C.] |
|---|---|---|---|---|---|---|
| | | | | % Calc. | % Found | |
| 4.5 | N | 4-F-C$_6$H$_4$-, 2-CH$_3$-pyrimidinyl | C | 60.87 | 60.5 | — |
| | | | H | 4.96 | 4.8 | |
| | | | N | 14.20 | 13.9 | |
| 4.6 | CH | 4-H$_3$CO-C$_6$H$_4$-, 2-CH$_3$-pyrimidinyl | C | 63.34 | 63.0 | 105–06 |
| | | | H | 5.46 | 5.2 | |
| | | | N | 11.98 | 12.1 | |
| 4.7 | N | 3-Cl-C$_6$H$_4$-pyrimidinyl | C | 58.92 | 58.7 | — |
| | | | H | 4.65 | 4.7 | |
| | | | N | 14.15 | 14.0 | |
| 4.8 | CH | 4-CH$_3$-C$_6$H$_4$-, 4,6-diCH$_3$-pyrimidinyl | C | 64.81 | 64.5 | — |
| | | | H | 5.59 | 5.3 | |
| | | | N | 12.26 | 12.2 | |
| 4.9 | CH | 4-CH$_3$-C$_6$H$_4$-, 5-C(CH$_3$)$_3$-, 6-CN-pyrimidinyl | C | 66.29 | 65.9 | 142–43 |
| | | | H | 5.70 | 5.5 | |
| | | | N | 11.60 | 11.5 | |
| 4.10 | CH | 2-pyridinyl | C | 62.07 | 62.1 | 133–34 |
| | | | H | 5.38 | 5.1 | |
| | | | N | 12.06 | 11.9 | |
| 4.11 | CH | 4-pyridinyl | C | 62.07 | 61.7 | |
| | | | H | 5.38 | 5.2 | |
| | | | N | 12.06 | 11.8 | |
| 4.12 | N | " | C | 59.90 | 59.6 | 110–11 |
| | | | H | 5.20 | 4.9 | |
| | | | N | 14.45 | 14.5 | |

TABLE 4-continued

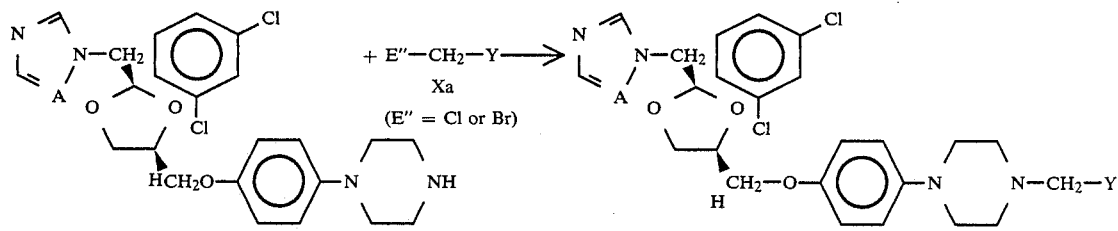

IXa (A = CH)
IXb (A = N)
cis cis I (Ar = 2,4-Cl$_2$—C$_6$H$_3$—, g = O)

| Comp. No. | A | Y | Analysis % Calc. | % Found | m.p. [°C.] |
|---|---|---|---|---|---|
| 4.13 | CH |  | C 64.76<br>H 5.28<br>N 11.11 | 64.5<br>5.0<br>10.8 | — |

EXAMPLE 18

According to principally the same procedure as described in Example 16, starting from 5 mmol of IXb and 5 mmol of 3-chloromethylpyridine hydrochloride, but in 25 ml of absolute dimethyl sulfoxide (DMSO) as solvent in place of DMF, and using an additional 2.5 mmol of powdered potassium carbonate (thus a total of 5 mmol of K$_2$CO$_3$), after appropriate work-up of the reaction mixture as described in Example 16, 1.80 g (62% of theory) of cis-2-(2,4-dichlorophenyl)-2-(1,2,4-triazol-1-ylmethyl)-4-[4-(4-(pyrid-3-ylmethyl)piperazin-1-yl)phenoxymethyl]-1,3-dioxolane, melting point 106°-107° C., were obtained; analysis: found C 59.6, H 5.0, N 14.3% (cf. Example 6, No. 2.23).

EXAMPLES OF THE PREPARATION OF COMPOUNDS OF THE FORMULA IIIa

EXAMPLE 19

A mixture of 4.94 g (14.5 mmol) of 1-(4-hydroxyphenyl)piperazine dihydrobromide, 3.29 g (14 mmol) of 4-chloromethyl-6-methoxy-2-phenylpyrimidine and 2.00 g (14.5 mmol) of powdered potassium carbonate in 50 ml of absolute N,N-dimethylformamide (DMF) was warmed to 80° C., and 322 mg of powdered K$_2$CO$_3$ were added with stirring under a nitrogen atmosphere in each case after 10 minutes, after a further 25 minutes, and after a further 60 minutes (total addition of 966 mg (7 mmol) of K$_2$CO$_3$). The mixture was stirred for a further 2.5 hours at 80° C., the DMF was substantially removed by distillation in an oil-pump vacuum in a rotary evaporator, the crystalline residue was mixed with 40 ml of water and 50 ml of CH$_2$Cl$_2$, the pH of the mixture was adjusted to 5-6 using 2N HCl, the phases were separated, and the aqueous phase was extracted three times with CH$_2$Cl$_2$. The combined CH$_2$Cl$_2$ extracts were dried, filtered and evaporated in vacuo. The residue (4.25 g) was chromatographed on a silica gel S/CH$_2$Cl$_2$ column (diameter 2.0 cm, height 23 cm) by elution with CH$_2$Cl$_2$ and CH$_2$Cl$_2$/C$_2$H$_5$OH mixtures, with increasing C$_2$H$_5$OH content (to a maximum of 4% by volume of C$_2$H$_5$OH). The fractions which were unary according to TLC were combined and crystallized from CH$_3$OH. In this fashion 3.06 g (≐58% yield) of 4-(4-hydroxyphenyl)-1-(6-methoxy-2-phenylpyrimidin-4-yl-methyl)piperazine were obtained; melting point 166°-67° C., analysis: C$_{22}$H$_{24}$N$_4$O$_2$ (MW 376.46) calc. C 70.19, H 6.43, N 14.88; found C 69.9, H 6.4, N 14.5%.

EXAMPLE 20

A mixture of 4.46 g (25 mmol) of 1-(4-hydroxyphenyl)piperazine and 5.52 g (25 mmol) of 6-chloromethyl-2-phenyl-4-pyrimidone in 90 ml of absolute N,N-dimethylformamide (DMF) was warmed to 80° C., and 576 mg of powdered K$_2$CO$_3$ was added with stirring under a nitrogen atmosphere in each case after 10 minutes, after a further 25 minutes, and after a further 60 minutes (total addition of 1.73 g (12.5 mmol) of K$_2$CO$_3$), and the mixture was stirred for a further 3.5 hours at 80° C. The DMF was then substantially removed by distillation in vacuo in a rotary evaporator,170 ml of water and 17 ml of 4N HCl were added to the residue, and the resultant mixture was extracted three times with CH$_2$Cl$_2$. The CH$_2$Cl$_2$ extract was discarded. The acidic aqueous solution was treated with activated charcoal, shaken thoroughly, and filtered under suction. The filtrate was neutralized using 2N NaOH. The crystalline precipitate precipitating during this was filtered off under suction, washed with water, boiled for 5 minutes with methanol, and, after cooling to 10°-15° C., filtered off under suction and dried. 6.25 g (≐69% yield) of pure 4-(4-hydroxyphenyl)-1-(2-phenyl-3,4-dihydropyrimidin-4-on-6-ylmethyl)piperazine hydrate, melting point 246°-48° C., were obtained, analysis: C$_{21}$H$_{24}$N$_4$O$_3$ (MW 380.45) calc. C 66.30, H 6.36, N 14.73; found C 65.9, H 6.1, N 14.5%.

EXAMPLE 21

According to the same procedure as described in Example 20, starting from 3.39 g (19 mmol) of 1-(4-hydroxyphenyl)piperazine and 4.20 g (17.9 mmol) of 6-chloromethyl-3,4dihydro-3-methyl-2-phenylpyrimidin-4-one, using 1.24 g (9 mmol) of K$_2$CO$_3$, 4.42 g (≐65.6% yield) of 4-(4-hydroxyphenyl)-1-(3,4-dihydro-3-methyl-2-phenylpyrimidin-4-on-6-ylmethyl)piperazine were obtained; melting point 206°-207° C., analysis: C$_{22}$H$_{24}$N$_4$O$_2$ (MW 376.46) calc. C 70.19 H6.43 , N 14.88; found C 69.2, H 6.4, N 14.5%. For workup of the reaction mixture, the DMF had been evaporated off in vacuo, the residue had been taken up in water/CH$_2$Cl$_2$ and neutralized, and the CH$_2$Cl$_2$ extract residue had been crystallized from CH$_3$OH.

EXAMPLE 22

325 mg (in total 975 mg (7 mmol)) of powdered K$_2$CO$_3$ were added at 80° C. with stirring in each case after 10 minutes, after a further 30 minutes, and after a further 60 minutes to a mixture of 2.59 g (14.5 mmol) of 1-(4-hydroxyphenyl)piperazine and 3.90 g (14 mmol) of 2-(4-bromomethyl-1-phenyl)-4,6-dimethylpyrimidine in 40 ml of absolute DMF, and the mixture was stirred for a further 3 hours at 80°. After evaporation of the DMF in vacuo, the crystalline residue was taken up in about 50 ml of water, the mixture was neutralized, shaken for 20 minutes, and subsequently filtered under suction. The filtration residue was washed with water, and then refluxed for 5 minutes with 30 ml of CH$_3$OH. The cooled mixture was filtered under suction, and the solid was dried. 3.15 g ($\doteq$59.7% yield) of 4-(4-hydroxyphenyl)-1-(4-(4,6-dimethylpyrimidin-2-yl)benzyl)piperazine, melting point 165°–67° C., were obtained, analysis: C$_{23}$H$_{26}$N$_4$O (MW 374.49) calc. C 73.77, H 7.00, N 14.96; found C 73.6, H 7.0, N 14.7%.

EXAMPLE 23

The compounds of the formula IIIa listed in Table 5 were prepared according to the procedures described in Examples 19–22, starting from a compound of the formula XIVa and in each case the appropriate bromomethyl or chloromethyl compound of the formula X (E″=Br or Cl; Y cf. Table 5).

If the residue remaining after removal of the DMF by distillation produced a crystalline product on taking-up in water and neutralization, it was further worked up as described in Example 22. If no crystalline substance was produced at this point, the residue was extracted with CH$_2$Cl$_2$. The CH$_2$Cl$_2$ extract residue was crystallized from CH$_3$OH or CH$_3$CN. If a crystalline substance could not be obtained in this way or if the substance produced was too greatly contaminated, the CH$_2$Cl$_2$ extract residue was purified chromatographically on a silica gel S/CH$_2$Cl$_2$ column by elution with CH$_2$CL$_2$ and CH$_2$Cl$_2$/C$_2$H$_5$OH mixtures. Compounds of the formula IIIa contained in Table 5 which were purified by chromatography are labeled "*".

TABLE 5

XIVa + X → IIIa (E″ = Br or Cl; Y, cf. Table)

| Comp. No. | R$^1$ | Y | Yield: [%] | m.p. [°C.] | Empirical formula | Analysis % Calc. | Found |
|---|---|---|---|---|---|---|---|
| 5.1 | H | (pyrimidinone-phenyl-Cl) | 71 | 269–70 | C$_{21}$H$_{23}$ClN$_4$O$_3$* | C 60.79<br>H 5.59<br>N 13.50 | 60.2<br>5.7<br>13.1 |
| 5.2 | H | OC$_4$H$_9$ (pyrimidine-phenyl) | 69 | 146–47 | C$_{25}$H$_{30}$N$_4$O$_2$ | C 71.74<br>H 7.22<br>N 13.39 | 71.6<br>7.0<br>13.3 |
| 5.3* | CH$_3$ | OCH$_3$ (pyrimidine-phenyl) | 62 | 119–20 | C$_{24}$H$_{28}$N$_4$O$_2$ | C 71.26<br>H 6.98<br>N 13.85 | 71.0<br>7.0<br>13.8 |
| 5.4* | H | (phenyl-imidazoline-CH$_3$) | 57 | 250–52 | C$_{22}$H$_{24}$N$_4$O | C 73.31<br>H 6.71<br>N 15.54 | 73.1<br>6.5<br>15.3 |
| 5.5* | CH$_3$ | " | 55 | 185–86 | C$_{24}$H$_{28}$N$_4$O | C 74.20<br>H 7.26<br>N 14.42 | 74.3<br>7.2<br>14.1 |

TABLE 5-continued $$\text{XIVa} + \text{E}''-\text{CH}_2-\text{Y} \longrightarrow \text{IIIa}$$

(E″ = Br or Cl; Y, cf. Table)

| Comp. No. | R¹ | Y | Yield: [%] | m.p. [°C.] | Empirical formula | Analysis % Calc. | Found |
|---|---|---|---|---|---|---|---|
| 5.6* | H | (4-methylphenyl)-2-ethyl-pyrimidine | 35 | 192–93 | $C_{23}H_{26}N_4O$ | C 73.77<br>H 7.00<br>N 14.96 | 73.8<br>7.1<br>14.7 |
| 5.7 | H | (4-methylphenyl)-5-OCH₃-2-CH₃-pyrimidine | 68 | 175–76 | $C_{23}H_{26}N_4O_2$ | C 70.74<br>H 6.71<br>N 14.35 | 70.8<br>6.6<br>14.3 |
| 5.8* | H | (4-methylphenyl)-5-CN-2-CH₃-pyrimidine | 51 | 234–35 | $C_{23}H_{23}N_5O$ | C 71.67<br>H 6.01<br>N 18.17 | 71.3<br>5.9<br>17.9 |
| 5.9* | H | 2-CH₃-pyrimidine | 63 | — | $C_{16}H_{20}N_4O$ | C 67.58<br>H 7.09<br>N 19.70 | 67.2<br>6.9<br>19.3 |
| 5.10* | CH₃ | 4-C₃H₇-pyrimidine | 50 | — | $C_{20}H_{28}N_4O$ | C 70.55<br>H 8.29<br>N 16.46 | 70.0<br>8.2<br>16.0 |
| 5.11 | H | 2-phenyl-pyrimidine | 83 | 176–77 | $C_{21}H_{22}N_4O$ | C 72.81<br>H 6.40<br>N 16.17 | 72.5<br>6.2<br>15.9 |
| 5.12* | CH₃ | ″ | 56 | 165–67+ | $C_{23}H_{27}ClN_4O^+$ | C 67.22<br>H 6.62<br>Cl 8.63<br>N 13.63 | 67.1<br>7.1<br>9.1<br>12.8 |
| 5.13 | H | 2-(4-chlorophenyl)-pyrimidine | 66 | 208–09 | $C_{21}H_{21}ClN_4O$ | C 66.22<br>H 5.56<br>N 14.71 | 66.0<br>5.7<br>14.4 |
| 5.14 | H | 2-(3,4-dimethoxyphenyl)-pyrimidine | 62 | 179–80 | $C_{23}H_{26}N_4O_3$ | C 67.96<br>H 6.45<br>N 13.78 | 67.5<br>6.3<br>13.4 |

TABLE 5-continued

XIVa + X → IIIa
(E″ = Br or Cl; Y, cf. Table)

| Comp. No. | R¹ | Y | Yield: [%] | m.p. [°C.] | Empirical formula | Analysis % Calc. | Found |
|---|---|---|---|---|---|---|---|
| 5.15 | H | (4-phenyl-6-methyl-pyrimidin-5-yl-methyl, CH₃ substituent) | 80 | 202-03 | $C_{22}H_{24}N_4O$ | C 73.31<br>H 6.71<br>N 15.54 | 73.4<br>6.6<br>15.3 |
| 5.16 | CH₃ | (4-phenyl-6-propyl-pyrimidin-5-yl-methyl, C₃H₇ substituent) | 51 | 81-83 | $C_{26}H_{32}N_4O$ | C 74.97<br>H 7.74<br>N 13.45 | 74.7<br>7.8<br>13.4 |
| 5.17* | H | (4-(3,4-dimethoxyphenyl)-6-octyl-pyrimidin-5-yl-methyl, OCH₃, OCH₃, C₈H₁₇) | 73 | 145-46 | $C_{31}H_{42}N_4O_3$ | C 71.78<br>H 8.16<br>N 10.80 | 71.4<br>8.0<br>10.8 |
| 5.18* | H | (4-(3-chlorophenyl)-pyrimidin-5-yl-methyl, Cl) | 55 | 182-83 | $C_{21}H_{21}ClN_4O$ | C 66.22<br>H 5.56<br>N 14.71 | 66.1<br>5.7<br>14.6 |
| 5.19* | H | (4-(4-chlorophenyl)-2-methyl-pyrimidin-5-yl-methyl, Cl, CH₃) | 57 | 155-56 | $C_{22}H_{23}ClN_4O$ | C 66.91<br>H 5.87<br>N 14.19 | 66.8<br>5.8<br>14.2 |
| 5.20* | H | (4-(4-fluorophenyl)-2-methyl-pyrimidin-5-yl-methyl, F, CH₃) | 63 | 190-91 | $C_{22}H_{23}FN_4O$ | C 69.82<br>H 6.13<br>N 14.81<br>F 5.02 | 69.6<br>6.3<br>14.7<br>4.9 |

TABLE 5-continued

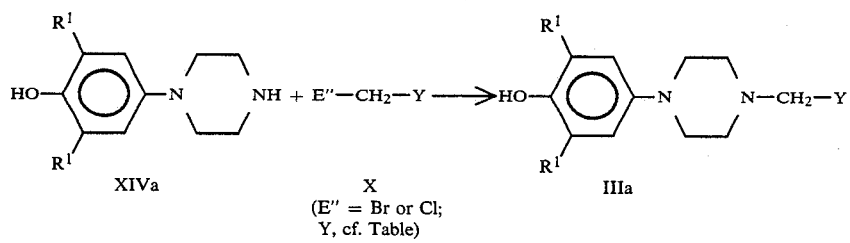

XIVa     X     IIIa
(E″ = Br or Cl; Y, cf. Table)

| Comp. No. | R¹ | Y | Yield: [%] | m.p. [°C.] | Empirical formula | Analysis % Calc. | Found |
|---|---|---|---|---|---|---|---|
| 5.21* | CH₃ | (cyclopentyl-ethyl-2-methylpyrimidine) | 59 | — | $C_{25}H_{36}N_4O$ | C 73.49<br>H 8.88<br>N 13.71 | 73.1<br>8.7<br>13.4 |
| 5.22* | H | (4-methoxyphenoxy-propyl-phenyl-pyrimidine) | 81 | 168–69 | $C_{31}H_{35}N_4O_3$ | C 72.77<br>H 6.90<br>N 10.95 | 72.2<br>6.8<br>10.6 |
| 5.23 | H | (dimethyl-N-methyl-phenyl-pyrimidinone) | 94 | 180–81 | $C_{23}H_{26}N_4O_2$ | C 70.74<br>H 6.71<br>N 14.35 | 70.5<br>6.6<br>14.1 |
| 5.24* | H | (propyl-methyl-N-methyl-phenyl-pyrimidinone) | 67 | 194–95 | $C_{25}H_{30}N_4O_2$ | C 71.74<br>H 7.22<br>N 13.39 | 71.8<br>7.1<br>13.2 |
| 5.25* | H | (2,4,6-trimethylpyrimidine) | 53 | 202–04 | $C_{17}H_{22}N_4O$ | C 68.43<br>H 7.43<br>N 18.78 | 68.3<br>7.4<br>18.7 |
| 5.26* | H | (4-methyl-2-phenylpyrimidine) | 79 | 163–64 | $C_{22}H_{24}N_4O$ | C 73.31<br>H 6.71<br>N 15.54 | 73.3<br>6.6<br>15.2 |

TABLE 5-continued

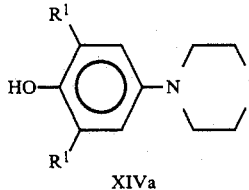

XIVa    X    IIIa
(E″ = Br or Cl;
Y, cf. Table)

| Comp. No. | R¹ | Y | Yield: [%] | m.p. [°C.] | Empirical formula | Analysis % Calc. | Found |
|---|---|---|---|---|---|---|---|
| 5.27* | H | 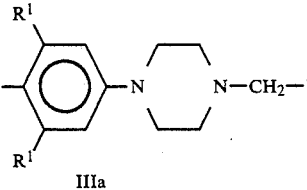 | 61 | 128–29 | $C_{25}H_{30}N_4O_2$ | C 71.74<br>H 7.22<br>N 13.39 | 71.5<br>7.2<br>13.3 |
| 5.28* | $CH_3$ | 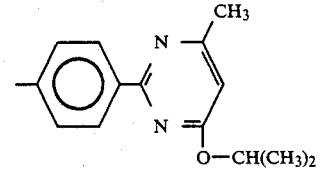 | 63 | 109–10 | $C_{25}H_{30}N_4O$ | C 74.59<br>H 7.51<br>N 13.92 | 74.6<br>7.4<br>13.7 |
| 5.29* | H | 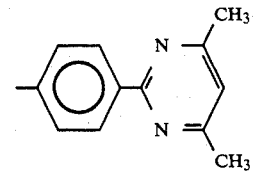 | 44 | — | $C_{28}H_{33}N_5O$ | C 73.81<br>H 7.30<br>N 15.37 | 73.6<br>7.1<br>15.1 |
| 5.30 | H | 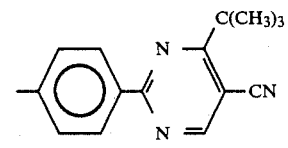 | 67 | 168–69 | $C_{16}H_{19}N_3O$ | C 71.35<br>H 7.11<br>N 15.60 | 71.3<br>7.0<br>15.5 |
| 5.31 | H | 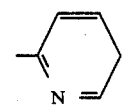 | 53 | 179–80 | $C_{22}H_{23}N_3O$ | C 76.49<br>H 6.71<br>N 12.17 | 76.5<br>6.6<br>12.1 |
| 5.32 | H | 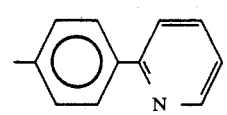 | 83 | 194–95 | $C_{16}H_{19}N_3O$ | C 71.35<br>H 7.11<br>C 15.60 | 71.2<br>7.0<br>15.6 |
| 5.33 | H | 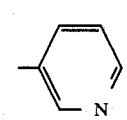 | 74 | 251–53 | $C_{16}H_{19}N_3O$ | C 71.35<br>H 7.11<br>N 15.60 | 71.1<br>7.1<br>15.4 |
| 5.34 | $CH_3$ | ″ | 56 | 156–57 | $C_{18}H_{23}N_3O$ | C 72.69<br>H 7.80<br>N 14.13 | 72.6<br>7.9<br>14.1 |
| 5.35* | H | 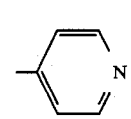 | 67 | 83–84 | $C_{20}H_{21}N_3O$ | C 75.21<br>H 6.63<br>N 13.16 | 75.3<br>6.6<br>13.0 |
| 5.36* | $CH_3$ | 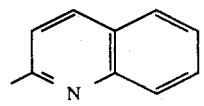 | 60 | — | $C_{22}H_{225}N_3O$ | C 76.05<br>H 7.25<br>N 12.09 | 75.7<br>7.0<br>11.7 |

TABLE 5-continued $R^1$, HO-phenyl-N(piperazine)NH + E″—CH₂—Y → $R^1$, HO-phenyl-N(piperazine)N—CH₂—Y XIVa + X → IIIa (E″ = Br or Cl; Y, cf. Table)

| Comp. No. | $R^1$ | Y | Yield [%] | m.p. [°C.] | Empirical formula | Analysis % Calc. | Found |
|---|---|---|---|---|---|---|---|
| 5.37 | H | (4-methyl-2-phenylpyrimidin-5-yl, dimethyl) | 83 | 115–16 | $C_{23}H_{26}N_4O$ | C 73.77<br>H 7.00<br>N 14.96 | 73.6<br>7.1<br>14.9 |
| 5.38 | H | (2-(4-chlorophenyl)-4,6-dimethylpyrimidin-5-yl) | 67 | 152–53 | $C_{23}H_{25}ClN_4O$ | C 67.55<br>H 6.16<br>N 13.70 | 67.2<br>6.2<br>13.3 |
| 5.39 | H | (2-phenylpyrimidin-5-yl) | 29 | 168–69 | $C_{21}H_{22}N_4O$ | C 72.81<br>H 6.40<br>N 16.17 | 72.6<br>6.2<br>16.2 |

*Hydrate
+hydrochloride

EXAMPLE 24

A solution of 1.05 g of triethylamine in 20 ml of absolute dimethoxyethane was added dropwise over 30 minutes with stirring to a mixture of 1.78 g (10 mmol) of 1-(4-hydroxyphenyl)piperazine, 3.05 g of 95% strength 5-bromomethyl-4-methyl-2-phenylpyrimidine ($\hat{=}$11 mmol) and 80 ml of absolute 1,2-dimethoxyethane at 45° C. The mixture was stirred for a further 1 hour at 45° C. and 3 hours at 80° C., the solvent was evaporated in vacuo, the residue was taken up in $CH_2Cl_2$ water and neutralized to pH 6–7, the phases were separated, and the aqueous phase was extracted three times with $CH_2Cl_2$. The combined $CH_2Cl_2$ extracts were dried, filtered and evaporated in vacuo. The crystalline residue (3.7 g) was recrystallized from methanol. 2.35 g (65% of theory) of pure 4-(4-hydroxyphenyl)-1-(4-methyl-2-phenylpyrimidin-5-ylmethyl)piperazine, melting point 201°–202° C., were obtained.

This synthesis may likewise be carried out using 1-(4-hydroxyphenyl)piperazine dihydrobromide. In this case, 3.10 g (30.7 mmol) of triethylamine are used in a 10 mmol batch, and the reaction time at 45° C. is extended to 12 hours, and that at 80° C. is extended to 6 hours. Approximately the same amount of pure 4-(4-hydroxyphenyl)-1-(4-methyl-2-phenylpyrimidin-5-ylmethyl)-piperazine are obtained as in the version above based on the piperazine derivative.

EXAMPLES OF THE PREPARATION OF BROMONETHYLPYRIMIDINES - STARTING MATERIALS FOR THE SYNTHESIS OF COMPOUNDS OF THE FORMULA IIIa

EXAMPLE 25

5.54 g (31.1 mmol) of N-bromosuccinimide (NBS) and 6 mg of dibenzoyl peroxide were added to a solution of 5.53 g (30 mmol) of 4,5-dimethyl-2-phenylpyrimidine in 110 ml of $CCl_4$, and the mixture was warmed to the boiling point for 5 minutes with stirring and irradiation with a daylight lamp with increased short-wave content (type: Osram UltraVitalux, 300 W, GUR 53). The NBS had then been consumed and converted into specifically light succinimide. It was filtered off under suction at room temperature and washed with a little $CCl_4$. The filtrate was evaporated in vacuo, the residue was dissolved in 100 ml of diisopropyl ether, the solution was clarified over kieselguhr, and the clear filtrate was again evaporated in vacuo. 7.70 g, 94.5% purity according to the $^1$H NMR spectrum, of 5-bromomethyl-4-methyl-2-phenylpyrimidine ($\hat{=}$92% yield), melting point 65°–66° C., were obtained, analysis: $C_{12}H_{11}BrN_2$ (MW 263.15) calc. C 54.77, H 4.21, Br 30.37, N 10.65; found C 53.5, H 3.9, Br 31.3, N 10.0%.

EXAMPLE 26

4.19 g (23.5 mmol) of NBS and 5 mg of dibenzoyl peroxide were added to a solution of 5.12 g (21.2 mmol) of 3,4-dihydro-3,5-dimethyl-2-phenyl-6-propylpyrimidin-4-one in 80 ml of $CCl_4$, and the mixture was warmed to the boiling point for 7 minutes with stirring and irradiation (cf. Example 25). The NBS had then been converted into succinimide. This was filtered off under suction and washed with $CCl_4$, and the filtrate was evaporated in vacuo. The residue was dissolved in n-pentane/diisopropyl ether 2:1, the turbid solution was clarified using kieselguhr, and the clear filtrate was again evaporated in vacuo to constant weight. According to the $^1H$ NMR spectrum, the residue (7.1 g) comprised 65% purity 5-bromomethyl-3,4-dihydro-3-methyl-2-phenyl-6-propylpyrimidin-4-one (or the corresponding 1,4-dihydro-1-methyl compound; cf. the pyrimidones mentioned for Y under $b_2$). This bromomethyl compound was reacted in this form with 1-(4-hydroxyphenyl)piperazine, with formation of the compound of the formula IIIa described in Example 23, Table 5, No. 5.24.

EXAMPLE 27

4.04 g (22.7 mmol) of NBS and 3 mg of dibenzoyl peroxide were added to a solution of 4.50 g (22.7 mmol) of 2-ethyl-4-(4-tolyl)pyrimidine in 90 ml of $CCl_4$, and the mixture was warmed to the boiling point for 3 minutes with stirring and irradiation (cf. Example 25). The NBS had then been converted into succinimide. After cooling to room temperature, this was filtered off under suction and washed with $CCl_4$, and the filtrate was evaporated in vacuo. The residue was dissolved in diisopropyl ether, the turbid solution was clarified using kieselguhr, and the clear filtrate was again evaporated in vacuo to constant weight. According to the $^1H$ NMR spectrum, the residue (5.83 g) comprised about 43% of 4-(4-bromomethyl phenyl)-2-ethylpyrimidine, about 34% of 2-(1-bromoethyl)-4-(4-tolyl)pyrimidine and about 23% of unreacted 2-ethyl-4-(4-tolyl)pyrimidine. This mixture was reacted with 1-(4-hydroxyphenyl)piperazine, with formation of the corresponding 4-(4-hydroxyphenyl)piperazine derivatives. The two structurally isomeric piperazine derivatives were separated by chromatography on a silica gel $S/CH_2Cl_2$ column, and the compound of the formula IIIa described in Example 23, Table 5, No. 5.6 was obtained in a pure form.

EXAMPLE 28

2.26 g (12.7 mmol) of NBS and 3 mg of dibenzoyl peroxide were added to a solution of 2.73 g (12.5 mmol) of 4-(4-chlorophenyl)-2,5-dimethylpyrimidine in 48 ml of $CCl_4$, and the mixture was refluxed for 5 minutes with stirring and irradiation (cf. Example 25). The NBS had then been converted into succinimide. This was filtered off at room temperature through a filtration aid and washed with $CCl_4$, and the filtrate was evaporated in vacuo. The residue was dissolved in about 60 ml of diisopropyl ether/n-pentane 1:1, the slightly turbid solution was clarified using kieselguhr and again filtered under suction, and the clear filtrate was evaporated in an oil-pump vacuum to constant weight. According to the $^1H$ NMR spectrum, the residue (3.4 g) comprised 69.5% purity 5-bromomethyl-4-(4-chlorophenyl)-2-methylpyrimidine (=63.5% yield). This bromomethyl compound was used in this form for the reaction with 1-(4-hydroxyphenyl)piperazine (cf. Example 23, No. 5.19).

EXAMPLE 29

3.61 g (yield=85% of theory) of 2-(4-bromomethylphenyl)pyridine, 82% purity according to the $^1H$ NMR spectrum, melting point 51°–52° C., were obtained as a crystalline evaporation residue by the procedure described in Example 28, starting from 2.37 g (14 mmol) of 2-(4-tolyl)pyridine in 80 ml of $CCl_4$, 2.60 g (14.6 mmol) of NBS and 3 mg of dibenzoyl peroxide. The bromomethyl compound was reacted in this form with 1-(4-hydroxyphenyl)piperazine with formation of the compound of the formula IIIa described in Example 23, No. 5.31.

The results of the treatment of laboratory animals infected experimentally with Trichophyton mentagrophytes are given as an example of the high local in vivo activity of the compounds according to the invention.

In order to determine the local activity, two guinea pigs (Pirbright white strain) weighing 450–500 g were each infected with $1.5 \times 10^4$ conidia/animal in the epidermis, distributed over 6 points of infection.

The animals were treated dermally from the 3rd day after the infection on 5 successive days by applying a 0.1% strength preparation solution to 3 points of infection on one back. The other back was treated in the same fashion with vehicle without the preparation.

In addition to the animals treated with the substances according to the invention, two animals were treated with the reference substance terconazole, and two animals were not treated after infection. As can be seen from Table 6, the compounds according to the invention exhibited a markedly greater reduction of the mycosis diameter than did the standard preparation terconazole, i.e the antimycotic effect of the compounds according to the invention was up to 60% superior to that of terconazole.

TABLE 6

| Concentration | Preparation Example No. | Vehicle controls | | | Preparation + vehicle | | | Difference |
|---|---|---|---|---|---|---|---|---|
| | | $x_1$ | (s)* | n** | $x_2$ | (s)* | n** | $x_1 - x_2$ (%) |
| Dermal | (6) 2.17 | 12.7 | (1.3) | 6 | 2.8 | (0.8) | 6 | 9.9 (157.1) |
| 5 × 0.1% | (3) | 14.0 | (1.2) | 6 | 4.3 | (1.5) | 6 | 9.7 (153.9) |
| | (6) 2.28 | 13.7 | (1.6) | 6 | 3.5 | (1.0) | 6 | 10.2 (161.9) |
| | terconazole | 13.9 | (1.2) | 6 | 7.6 | (1.4) | 6 | 6.3 (100) |
| Controls, untreated infected animals | — | 14.1 | (2.8) | 12 | — | | | — |

*(s) = Standard deviation
**n = Number of measurements

The results of the treatment of laboratory animals infected experimentally with Candida albicans are given as an example of the high oral and parenteral in vivo activity of the compounds according to the invention.

In order to determine the oral and parenteral activity, groups each comprising 5 mice weighing 18-20 g (strain HOE: NMRKF; SPF 71) were infected with $2 \cdot 10^6$ germs/animal.

The animals were treated orally or subcutaneously in 8 identical individual doses each of 30 mg/kg or 10 mg/kg of bodyweight (—24/—18-/—2h/+2/24/30/48/54h).

In addition to the group of 5 animals treated with the substances I according to the invention, a group, likewise of 5 animals, was treated for comparison with the reference substance ketoconazole. A control group of 10 animals was not treated after infection.

As can be seen from Table 7, the animals survived for up to about twice as long after infection in the case of the compounds according to the invention, compared to the current standard preparation ketoconazole.

TABLE 7

| Dose | Preparation Example No. | Number of animals | Survival times* days after infection | | | | | x days | Survival time in % (standard prep. = 100%) |
|---|---|---|---|---|---|---|---|---|---|
| oral 8 × 30 mg/kg | (6) 2.3 | 5 | 8 | 9 | 10 | 10 | 10 | 9.4 | 127.0 |
| | (6) 2.20 | 5 | 7 | 9 | 10 | 12 | 12 | 10.0 | 135.1 |
| | (6) 2.18 | 5 | 7 | 9 | 10 | 11 | 12 | 9.8 | 132.4 |
| | ketoconazole | 5 | 6 | 7 | 7 | 8 | 9 | 7.4 | 100 |
| oral 8 × 10 mg/kg | (6) 2.3 | 5 | 7 | 7 | 7 | 7 | 7 | 7.0 | 129.6 |
| | (6) 2.20 | 5 | 5 | 6 | 6 | 7 | 7 | 6.2 | 114.8 |
| | (6) 2.18 | 5 | 6 | 6 | 8 | 9 | 11 | 8.0 | 148.1 |
| | ketoconazole | 5 | 5 | 5 | 5 | 6 | 6 | 5.4 | 100 |
| subcutaneous 8 × 30 mg/kg | (6) 2.3 | 5 | 10 | 13 | 14 | 14 | 14 | 13.0 | 158.5 |
| | (6) 2.20 | 5 | 14 | 14 | 14 | 14 | 14 | 14.0 | 170.7 |
| | (6) 2.18 | 5 | 14 | 14 | 14 | 14 | 14 | 14.0 | 170.7 |
| | ketoconazole | 5 | 8 | 8 | 8 | 8 | 9 | 8.2 | 100 |
| subcutaneous 8 × 10 mg/kg | (6) 2.3 | 5 | 8 | 10 | 11 | 13 | 14 | 11.2 | 175 |
| | (6) 2.20 | 5 | 10 | 12 | 12 | 14 | 14 | 12.4 | 193.7 |
| | (6) 2.18 | 5 | 9 | 11 | 12 | 12 | 13 | 11.4 | 178.1 |
| | ketoconazole | 5 | 5 | 5 | 5 | 8 | 9 | 6.4 | 100 |
| Controls, untreated infected animals | — | 10 | 2 2 | 2 2 | 2 3 | 2 3 | 2 4 | 2.4 | 37.5 |

*Experiment terminated after 14 days

We claim:

1. A compound of the formula I

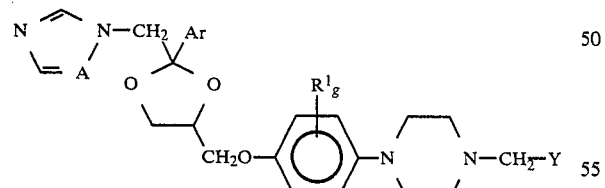

in which
A denotes CH or N,
Ar denotes naphthyl, thienyl, halothienyl or a phenyl group which is unsubstituted or carries one to 3 substituents, where the substituents may be identical or different and denote F, Cl, Br, I, CF$_3$, OCH$_3$, OC$_2$H$_5$, CH$_3$, C$_2$H$_5$ or phenoxy,
R$^1$ denotes C$_1$–C$_3$-alkyl, F or Cl,
g denotes 0, 1 or 2 and
Y denotes one of the following heterocyclic radicals

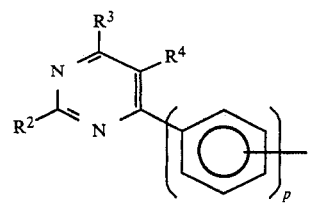 (a$_1$)

or

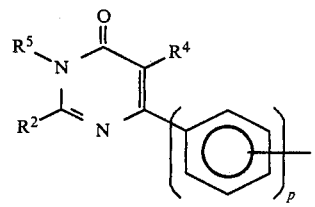 (a$_2$)

or

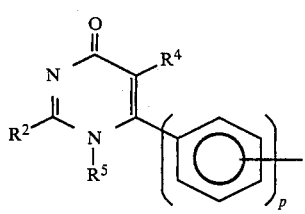

or

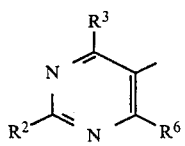 (b$_1$)

or (b$_2$)

or

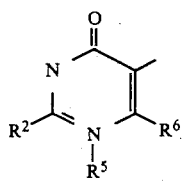

or

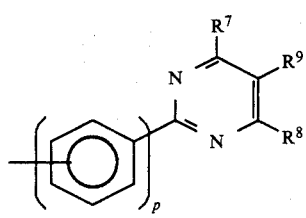

in which
R² denotes H, C₁–C₈-alkyl, C₁–C₄-alkoxy, a phenyl group which is unsubstituted or carries 1 or 2 substituents, where the substituents may be identical or different and denote F, Cl, Br, I, CF₃, OCH₃, OC₂H₅, NO₂ or C₁–C₄-alkyl, or a phenyl-C₁–C₂-alkyl group which is unsubstituted or carries 1 or 2 substituents in the phenyl radical, where the substituents may be identical or different and denote F, Cl, Br, OCH₃, OC₂H₅, CH₃ or C₂H₅, or, in the case of the radical a₁, additionally denotes C₁–C₄-alkylthio, or a benzylthio group which is unsubstituted or carries 1 or 2 substituents in the phenyl radical, where the substituents may be identical or different and denote F, Cl, OCH₃, OC₂H₅, CH₃ or C₂H₅, R³ denotes H, OH, Cl, C₁–C₄-alkoxy or a benzyloxy group which is unsubstituted or carries 1 or 2 substituents in the phenyl radical, where the substituents may be identical or different and denote note F, Cl, Br, OCH₃, OC₂H₅, CH₃ or C₂H₅, and, in the case of the heterocyclic radical a₁, additionally denotes C₁–C₄-alkyl or a phenyl group which is unsubstituted or substituted by one F, Cl, Br, OCH₃, OC₂H₅, CH₃ or C₂H₅ and, in the case of the heterocyclic radical b₁, additionally denotes C₁–C₄-alkyl or a phenyloxy group which is unsubstituted or carries 1 or 2 substituents, where the substituents may be identical or different and denote F, Cl, Br, OCH₃, OC₂H₅, CH₃ or C₂H₅, R⁴ denotes H, Cl, Br, C₁–C₄-alkyl or CN, R⁵ denotes H, C₁–C₄-alkyl, prop-2-en-1-yl, prop-2-in-1-yl or benzyl, P denotes 0 or 1, the phenylene radical in a₁, a₂ and c being bonded via the 2, 3 or 4 position, R⁶ denotes H, C₁–C₈-alkyl, (C₃–C₆-cycloalkyl)-C₁–C₃-alkyl, a phenyl group which is unsubstituted or carries 1 or 2 substituents, where the substituents may be identical or different and denote F, Cl, Br, I, OCH₃, OC₂H₅, 1,2——O—CH₂—O—, CF₃ or C₁–C₄-alkyl, a phenyl-C₁–C₂-alkyl group which is unsubstituted or substituted in the phenyl radical by OCH₃, OC₂H₅, 1,2—O—Ch₂—O—, CF₃, F, Cl, or C₁–C₄-alkyl or CF₃, R⁷ and R⁸ independently of one another, denote H, C₁–C₈-alkyl, C₁–C₄-alkoxy or a phenyl or benzyl group which is unsubstituted or carries 1 or 2 substituents in the phenyl radical, where the substituents may be identical or different and denote F, Cl, Br, OCH₃ or OC₂H₅, and where, in addition, R⁷ may alternatively denote OH, and R⁹ denotes H, Cl, Br or CN, and the physiologically acceptable acid-addition salts thereof.

2. A compound I as claimed in claim 1, wherein at least one of the substituents or indices has the following meaning:

A denotes CH or N,

Ar denotes a phenyl group which is substituted by 1 or 2 F or Cl atoms,

R¹ denotes CH₃ or C₂H₅, g denotes 0 or 2, and, where Y denotes a heterocyclic radical a₁, a₂,b₁, b₂ or c:

R² denotes H, C₁–C₄-alkyl, CH₃O or a phenyl or benzyl group is unsubstituted or carries 1 or 2 substituents in the phenyl radical, where the substituents may be identical or different and denote F, Cl, Br or OCH₃, R³ denotes H or C₁–C₄-alkoxy, and, in the case of the heterocyclic radical a₁, additionally denotes CH₃ or a phenyl group which is unsubstituted or substituted by one F, Cl, OCH₃ or CH₃, and, in the case of the radical b₁, additionally denotes a phenyloxy group which is unsubstituted or carries 1 or 2 substituents, where the substituents may be identical or different and denote F, Cl, Br, OCH₃ or OC₂H₅, R⁴ denotes H or CN, and, in the case of the heterocyclic radical a₁, additionally denotes C₁–C₄-alkyl, R⁵ denotes CH₃, p denotes 0 or 1, R⁶ denotes H, C₁–C₈-alkyl, (C₅–C₆-cycloalkyl)-C₁–C₂-alkyl, a phenyl group which is unsubstituted or carries 1 or 2 substituents, where the substituents may be identical or different and denote F, Cl, Br, OCH₃, OC₂H₅ or CF₃, a benzyl group which is unsubstituted or substituted in the phenyl radical by OCH₃, CF₃, F or Cl, or CF₃, R⁷ and R⁸, independently of one another, denote C₁–C₈-alkyl, C₁–C₄-alkoxy, or a phenyl or benzyl group which is unsubstituted or substituted in the phenyl radical by F, Cl, OCH₃ or OC₂H₅, and in addition, R⁷ alternatively denotes H or OH, and R⁹ denotes H or CN.

3. A compound I as claimed in claim 1, wherein at least one of the substituents or indices has the following meaning:

A denotes CH or N,

Ar denotes 2,4-dichlorophenyl,

R¹ denotes CH₃, g denotes 0 or 2, and, where Y denotes a heterocyclic radical a₁, a₂, b₁, b₂or c:

R²denotes CH₃, or a phenyl or benzyl group which is unsubstituted or carries 1 or 2 substituents in the phenyl radical, where the substituents may be identical or different and denote F or Cl, and, in the phenyl group, and in the phenyl and the benzyl group in the radical a₁, additionally denotes OCH₃, and, in the case of the radical a₁, additionally denotes C₂–C₄-alkyl, R³, in the radical a₁, if p is 0, denotes CH₃, or a phenyl group which is unsubstituted or substituted by an F, Cl or OCH₃, and, if p is 1, denotes H, and, in the radical b₁, denotes H or a phenyloxy group which is substituted by OC₂H₅, $R^4$ denotes H, or, in the radical $a_1$, additionally denotes $CH_3$ if p is 0,
$R^5$ denotes $CH_3$,
p denotes 0 or 1 in the case of the heterocyclic radicals $a_1$ and $a_2$, and denotes 1 in the case of the heterocyclic radical c,
$R^6$ denotes H, $CH_3$, or a phenyl group which is unsubstituted or monosubstituted by F, Cl, $OCH_3$ or $OC_2H_5$,
$R^7$ and $R^8$ and independently of one another, denote $CH_3$ or a phenyl group which is unsubstituted or substituted by F, Cl or $OCH_3$, and, in addition, $R^7$ alternatively denotes H or $C_1$–$C_4$-alkoxy, and
$R^9$ denotes H, the radical $d_4$ preferably being bonded via the 2 position and the radical $d_5$ preferably being bonded via the 6 or 7 position.

4. A compound I as claimed in claim 1, wherein the azolylmethyl radical and the piperazinophenoxymethyl group in the 4 position on the dioxolane ring are in the cis position.

5. A pharmaceutical composition comprising an amount effective for use as a pharmaceutical in the therapy of a mammal of at least one compound of the formula I as claimed in claim 1 or a physiologically acceptable acid-addition salt thereof.

6. A process for the treatment of mycosis, which comprises administering to a host in need of such treatment an effective amount of a pharmaceutical composition as claimed in claim 5.

7. A process for the treatment of mycosis which comprises administering to a host in need of such treatment an effective amount of at least one compound of the formula I as claimed in claim 1 or a phusiologically acceptable acid-addition salt thereof.

* * * * *